(12) United States Patent
Lubisch et al.

(10) Patent No.: US 6,696,437 B1
(45) Date of Patent: Feb. 24, 2004

(54) HETEROCYCLICALLY SUBSTITUTED BENZIMIDAZOLES, THE PRODUCTION AND APPLICATION THEREOF

(75) Inventors: Wilfried Lubisch, Heidelberg (DE); Michael Kock, Schifferstadt (DE); Thomas Hoeger, Edingen-Neckarhausen (DE); Roland Grandel, Dossenheim (DE); Uta Holzenkamp, Lambsheim (DE); Sabine Schult, Speyer (DE); Reinhold Mueller, Schifferstadt (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/959,632

(22) PCT Filed: Apr. 27, 2000

(86) PCT No.: PCT/EP00/03813
§ 371 (c)(1),
(2), (4) Date: Mar. 25, 2002

(87) PCT Pub. No.: WO00/68206
PCT Pub. Date: Nov. 16, 2000

(30) Foreign Application Priority Data

May 7, 1999 (DE) .......................................... 199 20 936

(51) Int. Cl.$^7$ ................... C07D 401/04; C07D 401/14; C07D 403/02; A61K 31/4184; A61K 31/454
(52) U.S. Cl. ................. 514/217.09; 514/249; 514/256; 514/255.05; 514/365; 514/367; 514/374; 514/378; 514/383; 514/307; 514/314; 514/300; 514/248; 514/252.03; 514/266.23; 514/218; 514/254.06; 514/234.5; 514/322; 514/338; 514/394; 544/333; 544/353; 544/405; 544/237; 544/238; 544/284; 544/370; 544/139; 546/144; 546/167; 546/199; 546/273.4; 548/215; 548/257; 548/240; 548/305.1; 548/305.4; 548/304.7; 548/306.1; 548/310.7; 540/575; 540/603

(58) Field of Search .................................. 544/333, 405, 544/353, 237, 238, 284, 370, 139; 514/256, 255.05, 249, 365, 367, 374, 378, 383, 314, 307, 300, 248, 252.06, 266.23, 218, 217.09, 254.06, 234.5, 322, 338, 394; 548/257, 215, 240, 305.1, 305.4, 304.7, 306.1, 310.7; 546/167, 144, 113, 194, 273.4

(56) References Cited

PUBLICATIONS

Chalmers (TiPS Vol 17, pp. 166–172 Apr. 1996).*

Chaby (Drug Discovery Today 4(5) 209–221, May 1999).*

Opal et al (Infectious Disease Clinics of North America 13(2), pp. 285–297, Jun. 1999).*

R. I. Souhami and J. Moxham ed.; "Textbook of Medicine" (Oct. 2002, Churchill Livingston, UK), see Chapter 4 pp. 79–104 by David Edgar and Herb Sewell.*

* cited by examiner

*Primary Examiner*—Mukund J. Shah
*Assistant Examiner*—Kahsay Habte
(74) *Attorney, Agent, or Firm*—Wood, Phillips, Katz, Clark & Mortimer

(57) ABSTRACT

The present invention relates to novel benzimidazoles, their preparation and their use as inhibitors of the enzyme poly (ADP-ribose) polymerase or PARP (EC 2.4.2.30) for producing drugs.

22 Claims, No Drawings

HETEROCYCLICALLY SUBSTITUTED BENZIMIDAZOLES, THE PRODUCTION AND APPLICATION THEREOF

The present invention relates to novel benzimidazoles, their preparation and their use as inhibitors of the enzyme poly-(ADP-ribose) polymerase or PARP (EC 2.4.2.30) for producing drugs.

Poly(ADP-ribose) polymerase (PARP) or, as it is also known, poly(ADP-ribose) synthase (PARS), is a regulatory enzyme found in cell nuclei (K. Ikai et al., *J. Histochem. Cytochem.* 1983, 31, 1261–1264). It is assumed that PARP is involved in the repair of DNA breaks (M. S. Satoh et al., *Nature* 1992, 356, 356–358). Damage or breaks in DNA strands activate the enzyme PARP which, when it is activated, catalyzes the transfer of ADP-ribose from NAD (S. Shaw, *Adv. Radiat. Biol.*, 1984, 11, 1–69). During this, nicotinamide is released from NAD. Nicotinamide is converted back into NAD by other enzymes with consumption of the energy carrier ATP. Overactivation of PARP would accordingly result in a nonphysiologically large consumption of ATP, and this leads in the extreme case to cell damage and cell death.

It is known that free radicals such as superoxide anion, NO and hydrogen peroxide may lead to DNA damage in cells and thus activate PARP. The formation of large amounts of free radicals is observed in a number of pathophysiological states, and it is assumed that this accumulation of free radicals leads or contributes to observed cell or organ damage. This includes, for example, ischemic states of organs as in stroke, myocardial infarct (C. Thiemermann et al., *Proc. Natl. Acad. Sci. USA*, 1997, 94, 679–683) or ischemia of the kidneys, but also reperfusion damage has occurred, for example, after lysis of myocardial infarct (see above: C. Thiemermann et al.). Inhibition of the enzyme PARP might accordingly be a means of at least partly preventing or moderating this damage. PARP inhibitors might thus represent a novel therapeutic principle for treating a number of diseases.

The enzyme PARP influences the repair of DNA damage and might thus also play a part in the therapy of cancers since a greater action potential on tumor tissue was observed (G. Chen et al. *Cancer Chemo. Pharmacol.* 1988, 22, 303) in combination with substances with cytostatic activity. Nonlimiting examples of tumors are leukemia, glioblastomas, lymphomas, melanomas and carcinomas of the breast and cervix.

In addition, it has been found that PARP inhibitors may show an immunosuppressant effect (D. Weltin et al. *Int.J.Immunopharmacol.* 1995, 17, 265–271).

It has likewise been discovered that PARP is involved in immunological disorders or diseases in which the immune system plays an important part, such as, for example, rheumatoid arthritis and septic shock, and that PARP inhibitors may show a beneficial effect on the course of the disease (H. Kröger et al. *Inflammation* 1996, 20, 203–215; W. Ehrlich et al. *Rheumatol. Int.* 1995, 15, 171–172; C. Szabo et al., *Proc. Natl. Acad. Sci. USA* 1998, 95, 3867–3872; S. Cuzzocrea et al. *Eur. J. Pharmacol.* 1998, 342, 67–76). PARP is understood to include for the purpose of this invention isoenzymes of the PARP enzyme described above.

In addition, the PARP inhibitor 3-aminobenzamide showed protective effects in a model of circulatory failure (S. Cuzzocrea et al., *Br. J. Pharmacol.* 1997, 121, 1065–1074).

There is likewise experimental evidence that inhibitors of the enzyme PARP might be useful as agents for treating diabetes mellitus (V. Burkart et al. *Nature Med.* 1999, 5, 314–319).

Benzimidazoles have been described many times. Thus, DE 38 30 060 discloses alkylated derivatives as inhibitors of erythrocyte aggregation. DE 35 22 230 mentions an ester derivative of 2-phenylbenzimidazole as inhibitor of platelet aggregation. Halogen-substituted 2-phenylbenzimidazoles having substituted amine radicals on the phenyl ring have been described in WO 98/06703 as MCP-1 antagonists.

Likewise known are 2-phenylbenzimidazoles in which the benzimidazole group is substituted by an amide group. 5-amido derivatives of 2-phenylbenzimidazole with alkyloxy radicals on the phenyl ring have been described in WO 94/12461 as inhibitors of cAMP phosphodiesterase. It was found in DE 35 46 575 (e.g. Example 15) for analogous derivatives that these compounds induce positive inotropic effects. 4-Amido derivatives having a pyridyl radical in position 3 are likewise mentioned in WO 97/48697 as inhibitors of cAMP phosphodiesterase.

Benzimidazoles with amido groups in position 4 and with heterocyclic rings in position 2 are likewise known, for example from Denn W. A. et al., J. Med. Chem. 1990, 33, 814–819. Described therein are, for example, benzimidazoles with thiophene ring, with pyridine rings, furan rings and pyrrole rings in position 2, although the amido groups in position 4 on the benzimidazole carry other alkylamino radicals, which is important for the cytotoxic effect mentioned therein, but these substitutions on the amide residue are extremely unfavorable for an inhibitory effect on the enzyme PARP and usually lead to inactive compounds (see page 728 in M. J. Suto et al., Drugs of the Future, 1991, 16, 723–739).

The synthesis of 2-phenyl-benzimidazole-4-carboxamides has been described in J. Chem. Soc. Perkin Trans 1, 1979, 2303–2307. Analogous compounds which have a substituted alkyl chain on the amide residue and are said to have a cytotoxic effect are mentioned in J. Med. Chem. 1990, 33, 814–819. WO 97/04771 mentions, on the other hand, benzimidazole-4-carboxamides which inhibit PARS. In particular, derivatives described therein as active have a phenyl ring in position 2, and the phenyl ring may also be substituted by simple substituents such as nitro, methoxy and $CF_3$. Although some of these substances show good inhibition of the enzyme PARP, the derivatives described therein have the disadvantage that they show little or no solubility in aqueous solutions and thus cannot be administered as aqueous solution.

In a number of therapies, such as stroke, the active ingredients are administered intravenously as infusion solution. For this purpose it is necessary to have available substances, in this case PARP inhibitors, which have adequate solubility in water at physiological pH values or close pH values (for example pH values of 5–8) so that an infusion solution can be prepared. Many of the PARP inhibitors described, especially the more effective PARP inhibitors, have the disadvantage, however, that they have only low or no solubility in water at these pH values and thus are not suitable for intravenous administration. Active ingredients of this type can be administered only with excipients intended to confer solubility in water (cf. WO 97/04771). These excipients, for example polyethylene glycol and dimethyl sulfoxide, frequently cause side effects or are not tolerated. Very effective PARP inhibitors with adequate solubility in water have not previously been described.

Benzimidazoles with a carboxylic ester group or a carboxamide group in position 5 and, at the same time, heteroaromatic rings in position 2 have seldom been described, examples being thiazoles (JP 4001631) and quinolines (WO 9820007). Benzimidazoles having, for example, methyl groups on the benzo ring, or having further benzo rings fused on the benzo ring, or even being unsubstituted thereon, have frequently been described with heteroaromatic rings in position 2, for example indoles (V. Ketarev et al., Chem. Heterocycl. Comp. 1980, 16, 501–506), quinolines (J. Gosh, J. Ind. Chem. Soc. 1938, 15, 89), pyridines (T. Hisano, Chem. Pharm. Bull 1982, 30, 2996–3004), Pyrimidines (H. Bredereck et al., Chem. Ber. 1960, 93, 2410–2414) and pyrroles (GB 966,796).

Benzimidazoles with heteroaromatic rings such as pyridine, furan, thiophene and pyrrole in position 2 and with carboxylic acid derivatives in position 4 have been described in W. A. Denny et al., J. Med. Chem. 1990, 33, 814–819 as potential cytostatics. However, the carboxylic acid derivatives prepared and mentioned in this case are only the carboxylic acid itself and amides with alkylamine residues on the N atom.

It has been found, surprisingly, that benzimidazoles also having heteroaromatic rings on the imidazole ring and having a primary carboxamide group in position 4, that is to say in contrast to W. A: Denny et al (see above) no other radicals on the amide N atom, are very effective inhibitors of the enzyme PARP. It is possible by further incorporation of chemical radicals such as aliphatic amines in addition to achieve distinctly improved water solubility by salt formation, for example with acids.

The present invention describes novel benzimidazole derivatives of the general formulae I and II which show advantages over the previously described compounds and are potent PARP inhibitors, some of which also show adequate solubility in water allowing administration as infusion solution.

The present invention relates to substituted benzimidazoles of the general formulae I and II:

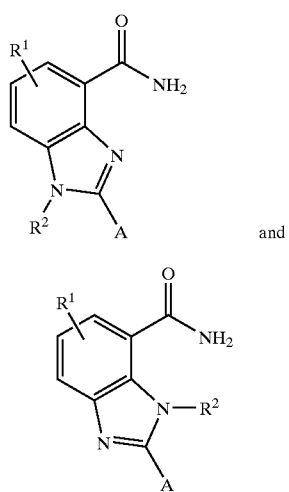

in which
A is napthalene, a monocyclic aromatic, bicyclic and tricyclic aromatic or partly aromatic heterocyclic system comprising a maximum of 15 carbon atoms and up to 4 heteroatoms selected from the group of N,O,S, and rings may additionally carry up to 2 oxo groups, and A may also be substituted by up to three different or identical $R^3$ radicals and additionally one $R^4$ radical, and $R^1$ is hydrogen, chlorine, fluorine, bromine, iodine, branched and unbranched $C_1$–$C_6$-alkyl, OH, nitro, $CF_3$, CN, $NR^{11}R^{12}$, NH—CO—$R^{13}$, O—$C_1$–$C_4$-alkyl, where $R^{11}$ and $R^{12}$ are, independently of one another, hydrogen or $C_1$–$C_4$-alkyl, and $R^{13}$ is hydrogen, $C_1$–$C_4$-alkyl, phenyl-$C_1$–$C_4$-alkyl or phenyl, and $R^2$ is hydrogen, branched and unbranched $C_1$–$C_6$-alkyl and $R^3$ is hydrogen, chlorine, bromine, iodine, fluorine, $CF_3$, $OCF_3$, nitro, $NH_2$, CO—$R^8$, $CO_2$—$R^8$, $SO_2$-$R^8$, OH, O—$C_1$–$C_4$-alkyl, phenyl-$C_0$–$C_4$-alkyl-O—, a $C_1$–$C_6$ chain which may be saturated, unsaturated or partially unsaturated and may also be substituted by an $R^{33}$ radical, phenyl, where the phenyl rings may also be substituted by up to three identical or different $R^{31}$ radicals, and pyridyl which may be substituted by up to three $R^{32}$ radicals, and $R^{31}$ is OH, $C_1$–$C_6$-alkyl, O—$C_1$–$C_4$-alkyl, chlorine, bromine, iodine, fluorine, $CF_3$, nitro, $NH_2$, and $R^{32}$ is OH, $C_1$–$C_6$-alkyl, O—$C_1$–$C_4$-alkyl, chlorine, bromine, iodine, fluorine, $CF_3$, nitro, $NH_2$, CN, and $R^{33}$ is CO—NH—$R^8$, OH, O—$C_1$–$C_6$-Alkyl, O—CO—$R^8$, and $R^4$ —(D)$_p$—(E)$_s$—(CH$_2$)$_q$ —B, where
D is S, $NR^{43}$ and O
E is phenyl and
s is 0 and 1 and
B is $NR^{41}R^{42}$ and

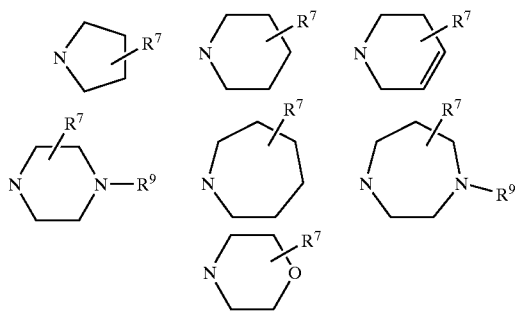

and
p can be 0 and 1, and
q can be 0, 1, 2, 3 or 4, and
$R^{41}$ can be hydrogen, $C_1$–$C_6$-alkyl, (CH$_2$)$_r$—G, and
$R^{42}$ can be hydrogen, $C_1$–$C_6$-alkyl, —CO—$R^8$, $SO_2$—$R^8$, $CO_2$—$R^8$, —(C=NH)—$R^8$ and —(C=NH)—NHR$^8$ and
$R^{41}$ and $R^{42}$ can form a phthaloyl radical and
$R^{43}$ can be hydrogen and $C_1$–$C_4$-alkyl and
r can be 0,1,2,3,4 and
G can be phenyl, which may also carry a maximum of two radicals R, $NR^{11}R^{12}$, phenyl-$C_1$–$C_4$-alkyl-NH, pyrrolidine, piperidine, 1,2,5,6-tetrahydropyridine, morpholine, homopiperidine, piperazine, which may also be substituted by an alkyl radical $C_1$–$C_6$-alkyl, and homopiperazine, which may also be substituted by an alkyl radical $C_1$–$C_6$-alkyl, and
$R^7$ can be hydrogen, $C_1$–$C_6$-alkyl, phenyl, it also being possible for the ring to be substituted by up to two $R^{71}$ radicals, and
$R^{71}$ can be OH, $C_1$–$C_6$-alkyl, O—$C_1$–$C_4$-alkyl, chlorine, bromine, iodine, fluorine, $CF_3$, nitro, $NH_2$, and
$R^8$ can be $C_1$–$C_6$-alkyl, $CF_3$, $NR^{11}R^{12}$, phenyl, phenyl-$C_1$–$C_4$-alkyl, it also being possible for the ring to be substituted by up to two $R^{81}$ radicals, and $R^{81}$ can be OH, $C_1$–$C_6$-alkyl, O—$C_1$–$C_4$-alkyl, chlorine, bromine, iodine, fluorine, $CF_3$, nitro, $NH_2$, and $R^9$ can be hydrogen, CO—$R^8$, $SO_2$—$R^8$, $CO_2$—$R^8$, $C_1$–$C_6$-alkyl, phenyl-$C_1$–$C_4$-alkyl and phenyl, it being possible for the phenyl ring also to be substituted by up to two $R^{91}$ radicals, and $R^{91}$ can be OH, $C_1$–$C_6$-alkyl, O—$C_1$–$C_4$-alkyl, chlorine, bromine, iodine, fluorine, $CF_3$, nitro, $NH_2$, and their tautomeric forms, possible enantiomeric and diastereomeric forms, and their prodrugs.

Preferred compounds of the formula I and II are those where $R^1$ can be hydrogen and $R^2$ can be hydrogen and $C_1$–$C_4$-alkyl and D can be $NR^{43}$ and O and p can be 0 and 1 and s can be 0 and q can be 0, 1 and 2, when p is 0, or q can be 2 and 3 when p is 1, and $R^{42}$ and $R^{43}$ can be, independently of one another, hydrogen and $C_1$–$C_4$-alkyl and $R^7$ can be hydrogen and phenyl and $R^9$ can be hydrogen, $C_1$–$C_4$-alkyl and phenyl-CO—$C_4$-alkyl.

Preferred meanings of A are indole, benzimidazole, pyrrole, imidazole, furan, thiophene, benzothiophene, benzofuran, pyrazole, thiazole, benzothiazole, phthalimide, indazole, benzotriazole, phthalazine, indoline, isoindoline, pyridine, quinoline, pyrimidine, pyridazine, isoquinoline, quinoxaline, quinazoline, naphthalene, isooxazole, oxazole, imidazopyridine, pyrazine.

Preferred compounds of the formula I and II are those where A has the following meaning:

pyridine, thiophene, thiazole, furan, indole, oxazole, pyrazole, pyrrole, benzofuran, imidazole, benzothiophene, isoxazole, pyrazine, pyrimidine, pyridazine, quinoline and the heterocyclic system may be substituted by up to three $R^3$ radicals and one $R^4$ radical, where $R^3$ is hydrogen, chlorine, bromine, iodine, fluorine, $COR^8$, $CO_2R^8$, $SO_2R^8$, a $C_1$–$C_6$ chain which may be saturated, unsaturated or partially saturated and may also be substituted by an O—CO—$R^8$ group, or phenyl-$C_1$–$C_6$-alkyl, phenyl, where the phenyl rings may also be substituted by up to three identical or different $R^{31}$ radicals, and pyridyl which may be substituted by up to three $R^{32}$ radicals, and $R^4$ is hydrogen and $(D)_p$—$(E)_s$—$(CH_2)_q$—B, and $R^3$ and $R^4$ are not both hydrogen.

Preferred compounds of formula I and II are those where A has the following meaning:

pyridine, pyrazine, pyrimidine, pyridazine, quinoline, thiazole, thiophene, pyrrole and pyrazole and the heterocyclic system may be substituted by an $R^3$ radical and an $R^4$ radical, where $R^3$ is hydrogen, chlorine, bromine, iodine, fluorine, $C_1$–$C_4$-alkyl and $R^4$ is $(D)_p$—$(E)_s$—$(CH_2)_q$—B.

Particularly preferred compounds of formula I and II are those where A may be pyridine, thiophene and thiazole, and the heterocyclic system is substituted with an $R^4$ radical where $R^4$ is $(D)_p$—$(E)_s$—$(CH_2)_q$—B, and $R^3$ is hydrogen.

The compounds of the formula I and II can be employed as racemates, as enantiomerically pure compounds or as diastereomers. If enantiomerically pure compounds are required, these can be obtained, for example, by carrying out a classical racemate resolution on the compounds of the formula I and II or their intermediates using a suitable optically active base or acid.

The invention also relates to compounds which are mesomers or tautomers of compounds of the formula I or II.

The invention further relates to the physiologically tolerated salts of the compounds I and II which can be obtained by reacting compounds I with a suitable acid or base. Suitable acids and bases are listed, for example, in Fortschritte der Arzneimittelforschung, 1966, Birkhäuser Verlag, volume 10, pp. 224–285. These include, for example, hydrochloric acid, citric acid, tartaric acid, lactic acid, phosphoric acid, methanesulfonic acid, acetic acid, formic acid, maleic acid, fumaric acid etc., and sodium hydroxide, lithium hydroxide, potassium hydroxide and tris.

Prodrugs mean compounds which are metabolized in vivo to compounds of the general formula I and II. Typical prodrugs are phosphates, carbamates of amino acids, esters and others.

Benzimidazoles I and II according to the invention can be prepared in various ways as outlined in synthesis schemes 1–3.

Synthesis Scheme 1

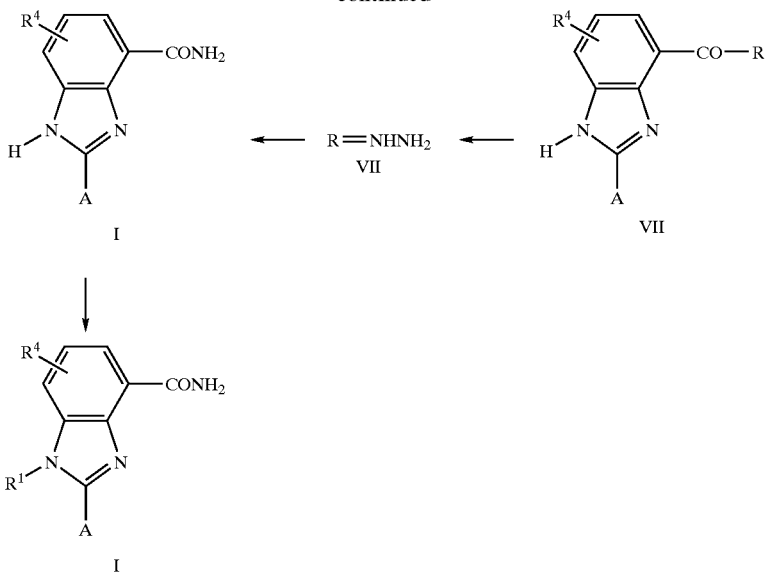

Condensation of the aldehyde with phenylenediamines gives the benzimidazole VII, this preferably being done in polar solvents such as ethanol or dimethylformamide with the addition of acids such as acetic acid at elevated temperature, usually 80 to 120° C. It is beneficial for the reaction to add weak oxidizing agents such as copper(II) salts, which are added as aqueous solution.

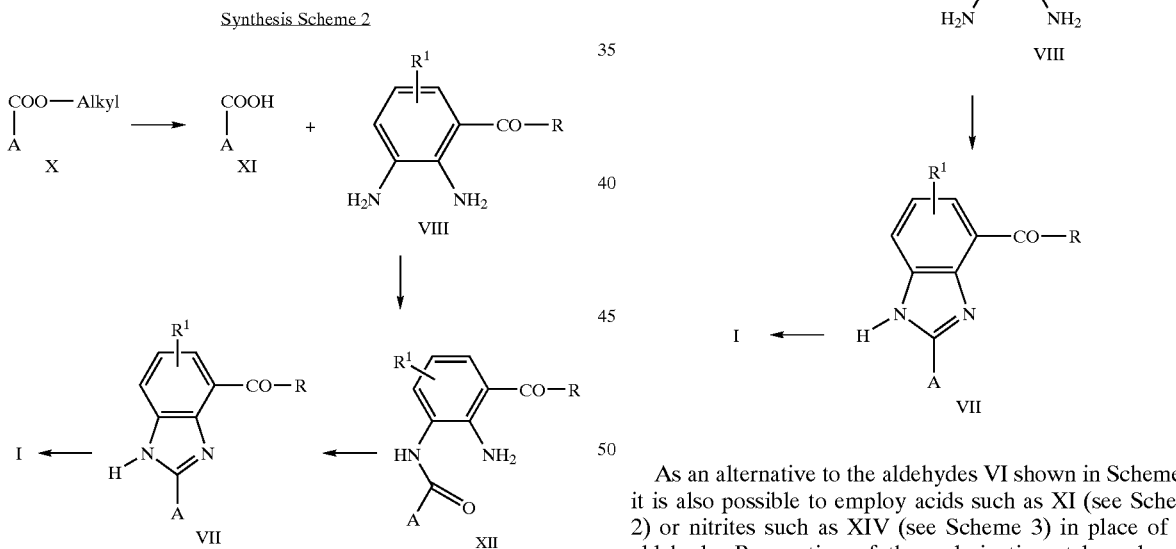

When R is $NH_2$ in the phenylenediamine VIII, the condensation directly results in compounds I according to the invention. Otherwise, if R is O-alkyl, this ester can be reacted with ammonia, where appropriate at elevated temperature and under elevated pressure, to give the amide I. Alternatively, the ester VIII can be reacted with hydrazine in polar solvents such as the alcohols butanol and ethanol or else dimethylformamide at elevated temperatures, preferably 80–130° C., to result in a hydrazide VIII (R=$NHNH_2$), which can then be reduced to the amide I under reducing conditions such as with Raney nickel in alcohols under reflux.

As an alternative to the aldehydes VI shown in Scheme 1, it is also possible to employ acids such as XI (see Scheme 2) or nitriles such as XIV (see Scheme 3) in place of the aldehyde. Preparation of these derivatives takes place in analogy to the preparation of the substituted aldehydes VI. Starting from XI, the condensation to VII takes place in two stages. Firstly the acid XI is reacted with the aniline VIII in a peptide-like coupling to give the amide XII. The usual conditions are employed for this, as listed, for example, in Houben-Weyl, Methoden der Organischen Chemie, 4th edition, E5, chapter V and R. C. Larock, Comprehensive Organic Transformations, VCH Publisher, 1989, page 972 et seq. The ring closure to the benzimidazole then takes place at elevated temperature, for example 60 to 180° C., with or without solvents such as dimethylformamide, with the addition of acids such as acetic acid or directly in acetic acid itself.

The reaction of the phenylenediamine VIII with a nitrile XIV likewise takes place under conventional conditions. This can be carried out in solvents such as dimethylformamide with the addition of acids or else in polyphosphoric acid at elevated temperature such as 60 to 200° C. However, it is also possible to use conventional methods for preparing amidines from benzonitriles as described in Houben-Weyl, Methoden der Organischen Chemie, E5, pp. 1304 et seq., J. Amer. Chem. Soc. 1957, 427 and J. Org. Chem. 1987, 1017.

The abovementioned substituted benzimidazoles I and II are inhibitors of the enzyme poly(ADP-ribose) polymerase or PARP (EC 2.4.2.30).

The inhibitory effect of the substituted benzimidazoles I and II can be determined using an enzyme assay disclosed in the literature, with a $K_i$ being determined as gauge of the effect. The benzimidazoles I and II were measured in this way for an inhibitory effect on the enzyme poly(ADP-ribose) polymerase or PARP (EC 2.4.2.30).

The substituted benzimidazoles of the general formulae I and II are inhibitors of poly(ADP-ribose) polymerase (PARP) or, as it is also known, poly(ADP-ribose) synthase (PARS), and can thus be used for the treatment and prophylaxis of diseases associated with an increased activity of these enzymes.

PARP isoenzymes are known in addition to the enzyme PARP, such as, for example, PARP II and PARP III (WO 99/64572).

The benzimidazoles I and II suprisingly also show an inhibitory effect on the enzyme PARP II.

A selective inhibition of PARP enzymes is desirable with a view to greater tolerability and fewer side effects of drugs.

Whereas the 2-phenylbenzimidazole-4-carboxamide (NU 1070) described in WO 97/04771 inhibits the enzymes PARP and PARP II with Ki values of the same order of magnitude, the benzimidazoles I and II show improved selectivities in the inhibition of PARP and PARP II.

The compounds of the formulae I and II can be employed to produce drugs for treating damage following ischemias and for the prophylaxis of expected ischemias in various organs.

The present benzimidazoles of the general formula I and II can accordingly be used for the treatment and prophylaxis of neurodegenerative disorders occurring after ischemia, trauma (craniocerebral trauma), massive bleeding, subarachnoid hemorrhages and stroke, and of neurodegenerative disorders such as multi-infarct dementia, Alzheimer's disease, Huntington's disease and of epilepsies, in particular of generalized epileptic seizures such as, for example, petit mal and tonoclonic seizures and partial epileptic seizures such as temporal lobe, and complex partial seizures, and further for the treatment and prophylaxis of damage to the heart after cardiac ischemias and damage to the kidneys after renal ischemias, for example of acute renal insufficiency, of acute kidney failure or of damage occurring during and after a kidney transplant. The compounds of the general formulae I and II can also be used to treat acute myocardial infarct and damage occurring during and after medical lysis thereof (for example with TPA, reteplase, streptokinase or mechanically with a laser or Rotablator) and microinfarcts during and after heart valve replacement, aneurysm resections and heart transplants. It is likewise possible to use the present benzimidazoles I and II for treatment in cases of revascularization of critically narrowed coronary arteries, for example in PTCA and bypass operations, and critically narrowed peripheral arteries, for example leg arteries. In addition, the benzimidazoles I and II can be beneficial in the chemotherapy of tumors and metastasis thereof and can be used to treat inflammations and rheumatic disorders such as, for example, rheumatoid arthritis, and for the treatment of diabetes mellitus.

The pharmaceutical preparations according to the invention comprise a therapeutically effective amount of the compounds I and II in addition to conventional pharmaceutical excipients.

For local external use, for example in dusting powders, ointments or sprays, the active ingredients can be present in the usual concentrations. The active ingredients are ordinarily present in an amount of from 0.001 to 1% by weight, preferably 0.001 to 0.1% by weight.

On internal use, the preparations are administered in single doses. From 0.1 to 100 mg are given per kg of bodyweight in a single dose. The preparations may be administered in one or more doses each day, depending on the nature and severity of the disorders.

Appropriate for their required mode of administration, the pharmaceutical preparations according to the invention comprise conventional carriers and diluents in addition to the active ingredient. For local external use it is possible to use pharmaceutical excipients such as ethanol, isopropanol, ethoxylated castor oil, ethoxylated hydrogenated castor oil, polyacrylic acid, polyethylene glycol, polyethylene glycol stearate, ethoxylated fatty alcohols, liquid paraffin, petrolatum and wool fat. Examples suitable for internal use are lactose, propylene glycol, ethanol, starch, talc and polyvinylpyrrolidone.

It is also possible for antioxidants such as tocopherol and butylated hydroxyanisole and butylated hydroxytoluene, flavor-improving additives, stabilizers, emulsifiers and lubricants to be present.

The substances present in the preparation in addition to the active ingredient, and the substances used in the production of the pharmaceutical preparations, are toxicologically acceptable and compatible with the particular active ingredient. The pharmaceutical preparations are produced in a conventional way, for example by mixing the active ingredient with conventional carriers and diluents.

The pharmaceutical preparations can be administered in various ways, for example orally, parenterally such as intravenously by infusion, subcutaneously, intraperitoneally and topically. Thus, possible presentations are tablets, emulsions, infusion and injection solutions, pastes, ointments, gels, creams, lotions, dusting powders and sprays.

EXAMPLE A

Inhibition of the Enzyme poly(ADP-ribose) Polymerase or PARP (EC 2.4.2.30)

a) ELISA

Materials:

ELISA color reagent: TMB mix SIGMA T-8540

A 96-well microtiter plate (FALCON Micro-Test IIIa Flexible Assay Plate, #3912) was coated with histones (SIGMA, H-7755). Histones were for this purpose dissolved in carbonate buffer (0.05 M $Na_2HCO_3$; pH 9.4) in a concentration of 50 µg/ml. The individual wells of the microtiter plate were each incubated with 150 µl of this histone solution at room temperature for at least 2 hours or at 4° C. overnight. The wells are then blocked by adding 150 µl of a 1% strength BSA solution (SIGMA, A-7888) in carbonate buffer at room temperature for 2 hours. This is followed by three washing steps with washing buffer (0.05% tween10 in 1×PBS; PBS (phosphate buffered saline; Gibco, Order No. 10010): 0.21 g/l $KH_2PO_4$, 9 g/l NaCl, 0.726 g/l Na$_2$HPO$_4$.7H$_2$O, pH 7.4). Washing steps were all carried out in a microtiter plate washer ("Columbus" microtiter plate washer, SLT-Labinstruments, Austria).

Required for the enzyme reaction were an enzyme reaction solution and a substrate solution, in each case as a premix. The absolute amount of these solutions depended on the intended number of assay wells.

Composition of the enzyme reaction solution per well:
 4 µl of PARP reaction buffer (1 M tris-HCl pH 8.0, 100 mM MgCl$_2$, 10 mM DTT)
 20 ng of PARP (human or bovine)
 4 µl of activated DNA (1 mg/ml; SIGMA, D-4522)
 ad 40 µl H$_2$O Composition of the substrate solution per well:
 5 µl of PARP reaction buffer (10×)
 0.8 µl of NAD solution (10 mM, SIGMA N-1511)
 44 µl of H$_2$O Inhibitors were dissolved in 1× PARP reaction buffer. DMSO, which was occasionally used to dissolve inhibitors in higher concentrations, was no problem up to a final concentration of 2%. For the enzyme reaction, 40µl of the enzyme reaction solution were introduced into each well and incubated with 10 µl of inhibitor solution for 10 minutes. The enzyme reaction was then started by adding 50 µl of substrate solution per well. The reaction was carried out at room temperature for 30 minutes and then stopped by washing three times with washing buffer.

The primary antibodies employed were specific anti-poly (ADP-ribose) antibodies in a dilution of 1:5000. Dilution took place in antibody buffer (1% BSA in PBS; 0.05% Tween20). Incubation time for the primary antibody was one hour at room temperature. After subsequently washing three times with washing buffer, incubation was carried out with the secondary antibody (anti-mouse IgG, Fab fragments, peroxidase-coupled, Boehringer Mannheim, Order No. 1500.686; anti-rabbit IgG, peroxidase-coupled, SIGMA, Order No. A-6154) in a 1:10,000 dilution in antibody buffer at room temperature for one hour. Washing three times with washing buffer was followed by the color reaction using 100 µl of color reagent (TMB mix SIGMA) per well at room temperature for about 15 min. The color reaction was stopped by adding 100 µl of 2M H$_2$SO$_4$. This was followed by immediate measurement in an ELISA plate reader (EAR340AT "Easy Reader", SLT-Labinstruments, Austria) (450 nm versus 620 nm).

Various concentrations were used to construct a dose-effect plot to determine the K$_i$ of an inhibitor. Values are obtained in triplicate for a particular inhibitor concentration. Arithmetic means are determined using Microsoft© Excel. The IC$_{50}$ is determined using the Microcal© Origin Software (Vers. 5.0) ("Sigmoidal Fit"). Conversion of the IC$_{50}$ values calculated in this way into K$_i$ values took place by using "calibration inhibitors". The "calibration inhibitors" were also measured in each analysis. The K$_i$ values of the "calibration inhibitors" were determined in the same assay system by analysis of the Dixon diagram in the manner familiar to the skilled worker.

b) HTRF (Homogeneous Time-resolved Fluorescence) Assay

In the HTRF PARP assay histones, as target proteins for modification by PARP, are labeled indirectly with an XL665 fluorophore. The antibody is directly labeled with a europium cryptate. If the XL665 fluorophore is in the direct vicinity in space, which is ensured by binding to the poly (ADP-ribose) on the histone, then energy transfer is possible. The emission at 665 nm is thus directly proportional to the amount of bound antibody, which in turn is equivalent to the amount of poly(ADP-ribose). The measured signal thus corresponds to the PARP activity. The materials used are identical to those used in the ELISA (see above) unless expressly stated.

Histones (Sigma M7755) were dissolved in a concentration of 3 mg/ml in Hepes buffer (50 mM, pH=7.5). Biotinylation took place with sulfo-NHS-LC-biotin (Pierce, #21335T). A molar ratio of 4 biotin per histone was used. The incubation time was 90 minutes (RT). The biotinylated histones were then purified on a G25 SF HR10/10 column (Pharmacia, 17-0591-01) in Hepes buffer (50 mM, pH=7.0) to remove excess biotinylation reagent. The anti-poly(ADP-ribose) antibody was labeled with europium cryptate using bifunctional coupling reagents (Lopez E. et al. Clin. Chem. 39/2, 196–201, 1993 U.S. Pat. No. 5,534,662). Purification took place on a G25SF HR10/30 column. A molar ratio of 3.1 cryptates per antibody was achieved. The yield was 25%. The conjugates were stored in the presence of 0.1% BSA in phosphate buffer (0.1 M, pH=7) at −80° C.

For the enzyme reaction, the following were pipetted into each well:
 10 µl of PARP solution in PARP HTRF reaction buffer (50 mM tris-HCl pH 8.0, 10 mM MgCl$_2$, 1 mM DTT) with 20 ng of PARP (human or bovine)
 10 µl of activated DNA (SIGMA D4522) in PARP HTRF reaction buffer (50 µg/ml)
 10 µl of biotinylated histones in PARP HTRF reaction buffer (1.25 µM)
 10 µl of inhibitor in PARP HTRF reaction buffer These reagents were preincubated for 2 minutes before starting the reaction by adding
 10 µl of NAD solution in PARP HTRF reaction buffer (400 µM). The reaction time was 30 minutes at room temperature.

The reaction was then stopped by adding
 10 µl of PARP inhibitor (25 µM, K$_i$=10 nM) in "Revelation" buffer (100 mM tris-HCl, pH 7.2, 0.2 M KF, 0.05% BSA)

The following were then added:
 10 µl of EDTA solution (SIGMA, E-7889, 0.5 M in H$_2$O)
 100 µl of Sa-XL665 (Packard Instruments) in "Revelation" buffer (15–31.25 nM)
 50 µl of anti-PARP cryptate in "Revelation" buffer (1.6–3.3 nM).

Measurement was then possible after 30 minutes (up to 4 hours). The measurement took place in a "Discovery HTRF Microplate Analyzer" (Packard Instruments). The K$_i$ values were calculated as described for the ELISA.

EXAMPLE B

Determination of the Solubility in Water

A compound to be measured is dissolved directly in a fixed volume of water, and the resulting solution is adjusted to pH 5–6 with a sodium acetate solution so that the active ingredient concentration to be tested is reached. If the measured substance is not in the form of a water-soluble salt, it was dissolved in the minimum amount of dimethyl sulfoxide and then diluted with water (final dimethyl sulfoxide concentration≦1%), after which the pH was again adjusted. The potent PARP inhibitor NU 1076 (WO 97/04771) showed a solubility <0.01%, whereas Example 1 according to the invention shows a solubility>0.5%.

The best PARP inhibitors of the invention are those of Examples 15, 16, 25, 36 and 37.

EXAMPLES

Example 1

2-Pyridin-4-ylbenzimidazole-4-carboxamide a) Ethyl 2-Pyridin-4-ylbenzimidazole-4-carboxylate 1 g (5.5 mmol) of ethyl 2,3-diaminobenzoate and 0.7 ml (11.3 mmol) of acetic acid were dissolved in 15 ml of ethanol. Then 0.77 g (7.2 mmol) of pyridine-4-carbaldehyde, dissolved in 25 ml of ethanol was added dropwise over the course of 30 minutes. A solution of 1.44 g (7.2 mmol) of copper(II) sulfate in 20 ml of water was then rapidly added dropwise. The mixture was boiled under reflux for 2 hours. The reaction solution was then allowed to cool to 50° C. 2.25 ml of 32% strength hydrochloric acid were then added. A solution of 2.13 g (8.9 mmol) of sodium sulfide hydrate and 25 ml of water was then cautiously added dropwise while hot. The mixture was stirred for 10 minutes. The reaction mixture was then poured into ice-water, and the resulting precipitate was filtered off. The filtrate was made alkaline with aqueous sodium bicarbonate solution and extracted with ethyl acetate. The organic phase was washed with water, dried and concentrated in vacuo. 1.15 g of the product were obtained.

b) 2-Pyridin-4-ylbenzimidazole-4-carbohydrazide 1 g (3.7 mmol) of the product 1a was dissolved in 30 ml of butanol. 6 ml of hydrazine hydrate were added and the mixture was boiled under reflux for 8 h. After cooling, the reaction solution was concentrated in vacuo. The residue was stirred with ether and filtered off with suction, resulting in 0.74 g of the product.

c) 2-Pyridin-4-ylbenzimidazole-4-carboxamide 0.7 g (2.8 mmol) of the product 1b and 1.5 g of Raney nickel (suspension in water) were heated in 45 ml of dimethylformamide/water (2/1) at 100° C. for 8 hours. After cooling and filtration, the filtrate was diluted with water, and the precipitate was then filtered off with suction. 0.16 g of the product was obtained.

$^1$H-NMR (D$_6$-DMSO): d=7.4 (1H), 7.85 (2H), 7.9 (1H), 8.2 (2H), 8.8 (2H) and 9.2 (1H)ppm.

Example 2

2-Pyridin-4-ylbenzimidazole-4-carboxamide×2 Methanesulfonic Acid 61 mg (0.26 mmol) of the compound from Example 1 were dissolved in 1 ml of tetrahydrofuran, and 25 mg (0.26 mmol) of methanesulfonic acid dissolved in 5 ml of water were added. The mixture was then diluted with water and freeze-dried. 58 mg of the product were obtained.

$^1$H-NMR (D$_6$-DMSO): δ=2.6 (3H), 6.9 (1H), 7.1 (1H), 7.3–7.5 (3H), 7.8 (1H), 8.1 (1H), 8.8 (1H), 9.0 (1H) and 9.1 (1H) ppm.

Example 3

2-(Benzimidazol-5-yl)benzimidazole-4-carboxamide a) 2-(Benzimidazol-5-yl)benzimidazole-4-carboxylic Acid 2 g (12 mmol) of methyl 2,3-diaminobenzoate and 2 g (12 mmol) of benzimidazole-5-carboxylic acid were successively introduced into 70 ml of polyphosphoric acid preheated to 90° C. The mixture was then heated at 200° C. for 1 hour. The reaction mixture was subsequently cooled to 50 to 60° C. and poured cautiously into ice-water. The resulting precipitate was filtered off with suction and dried. 2.7 g of the product were obtained.

b) Ethyl 2-(Benzimidazol-5-yl)benzimidazole-4-carboxylate 2.6 g (9.3 mmol) of the product 3a were stirred in 100 ml of ethanol and then 10 ml of concentrated sulfuric acid were cautiously added. The mixture was boiled under reflux for 1 hour. The reaction solution was then cautiously poured into ice-water. The resulting solution was made alkaline with aqueous sodium bicarbonate solution and extracted with ethyl acetate. The organic phase was separated off, dried and concentrated in vacuo. 2.7 g of the product were obtained.

c) 2-(Benzimidazol-5-yl)benzimidazole-4-carbohydrazide 2.6 g (8.5 mmol) of the product 3b were reacted with hydrazine hydrate in analogy to the process of 1b. 1.4 g of the product were obtained.

d) 2-(Benzimidazol-5-yl)benzimidazole-4-carboxamide 1.4 g of the product 3c were treated with Raney nickel in analogy to the process of 1c. 0.65 g of the product were obtained.

$^1$H-NMR (D$_6$-DMSO): δ=7.3 (1H), 7.7–7.9 (5H), 8.2 (1H), 8.4 (1H), 8.5 (1H) and 9.5 (1H) ppm.

Example 4

2-(1-(2-(N,N-Diethylamino)eth-1-yl)benzimidazol-5-yl)benzimidazole-4-carboxamide×3 HCl a) Ethyl 1-(2-(N,N-diethylamino)-1-ethyl)benzimidazole-5-carboxylate 5.4 g (28.4 mmol) of ethyl benzimidazole-5-carboxylate, 9.8 g (56.8 mmol) of N-(2-chloro-1-ethyl)-N,N-diethylamine and 7.9 g (56.8 mmol) of potassium carbonate were heated in 100 ml of dimethylformamide at 100° C. for 4 hours. The mixture was then filtered, the filtrate was concentrated in vacuo, and the resulting residue was purified by chromatography (mobile phase: ethyl acetate/acetone=1/1). 2.6 g of an isomer mixture containing ethyl 3-(2-(N,N-diethylamino)-1-ethyl)benzimidazole-5-carboxylate in addition to the product were obtained.

b) 1-(2-(N,N-Diethylamino)eth-1-yl)benzimidazole-5-carboxylic Acid×2 HCl 2.5 g (8.6 mmol) of the product 4a were dissolved in 50 ml of ethanol and, after addition of 50 ml of 1 M sodium hydroxide solution, boiled under reflux for 1 hour. After cooling, the reaction solution was neutralized with dilute hydrochloric acid and concentrated in vacuo. The residue obtained in this way was stirred with a mixture of tetrahydrofuran and methanol (1/1) and filtered. The filtrate was concentrated in vacuo, then dissolved in water and, after addition of two equivalents of hydrochloric acid, freeze-dried. 3.4 g of the isomer mixture were obtained.

c) Methyl 2-Amino-3-(1-(2-(N,N-diethylamino)eth-1-yl)benzimidazole-5-carboxamido)benzoate To 3.3 g (9.9 mmol) of the product 4b in 100 ml of anhydrous dimethylformamide at room temperature were successively added 1.6 g (9.9 mmol) of methyl 2,3-diaminobenzoate, 0.44 g (3.3 mmol) of N-hydroxybenzotriazole (HOBT) and 6.2 ml (44.4 mmol) of triethylamine. Then, at 15° C., 1.9 g (9.9 mmol) of N'-(3-dimethylaminopropyl)-N-ethylcarbodiimide (EDC) were added in portions. The mixture was stirred at room temperature for 16 hours. The reaction mixture was then concentrated in vacuo. The residue was partitioned between water and ethyl acetate. The aqueous phase was separated off, made alkaline with aqueous sodium bicarbonate solution and extracted with ethyl acetate. This organic phase was separated off, treated with active carbon, filtered, dried and concentrated in vacuo. 1.5 g of the product were obtained as an isomer mixture.

d) Methyl 2-(1-(2-(N,N-diethylamino)eth-1-yl)benzimidazol-5-yl)benzimidazole-4-carboxylate 1.5 g of the product 4c were boiled under reflux in 75 ml of acetic acid for 1 hour. The mixture was then concentrated in vacuo. 2.2 g of the product were obtained.

e) 2-(1-(2-(N,N-Diethylamino)eth-1-yl)benzimidazol-5-yl)benzimidazole-4-carbohydrazide 2.2 g of the product 4d were reacted with hydrazine hydrate in analogy to process 1b. A crude product was obtained and was reacted further without purification.

f) 2-(1-(2-(N,N-Diethylamino)eth-1-yl)benzimidazol-5-yl)benzimidazole-4-carboxamide×3 HCl The product from 4e was treated with Raney nickel in analogy to process 1c. The crude product was finally dissolved in hot isopropanol, and a little isopropanolic hydrogen chloride solution was added. The product crystallized on cooling. 0.98 g of the isomer mixture was obtained. MS: m/e=376 (M$^+$).

Example 5

2-(1-(2-(N,N-Diethylamino)eth-1-yl)indol-3-yl)benzimidazole-4-carboxamide a) 1-(2-N,N-Diethylaminoeth-1-yl)indole-3-aldehyde 1.1 g (45.4 mmol) of sodium hydride (80% strength) were added in portions to a solution of 5 g (34.5 mmol) of indole-3-aldehyde in 100 ml of anhydrous tetrahydrofuran at 0° C. The mixture was then stirred for 15 minutes. 7.4 g (68.9 mmol) of N-(2-chloro-1-ethyl)-N,N-diethylamine dissolved in 50 ml of anhydrous tetrahydrofuran were then added dropwise. The mixture was subsequently stirred at room temperature for 16 hours. 40 ml of water were then added dropwise (N.B. sodium hydride) to the reaction solution, and the organic solvent was removed in vacuo. The remaining phase was diluted with water and extracted with ether. This organic phase was washed with 2 M hydrochloric acid and water, dried and concentrated in vacuo.

b) Methyl 2-(1-(2-(N,N-diethylamino)eth-1-yl)indol-3-yl)benzimidazole-4-carboxylate 1.9 g (7.8 mmol) of the product 5a and 1 g (6 mmol) of methyl 2,3-diaminobenzoate were reacted in analogy to method 1a. 1.5 g of the product were obtained.

c) 2-(1-(2-(N,N-Diethylamino)eth-1-yl)indol-3-yl)benzimidazole-4-carbohydrazide 1.5 g of the product 5b were reacted with hydrazine hydrate in analogy to method 1b. 0.39 g of the product was obtained.

d) 2-(1-(2-(N,N-Diethylamino)eth-1-yl)indol-3-yl)benzimidazole-4-carboxamide 0.35 g of the product 5c were treated with Raney nickel in analogy to method 1c. 0.14 g of the product was obtained.

$^1$H-NMR (D$_6$-DMSO): δ=1.1 (3H), 2.8–3.2 (6H), 4.6 (2H), 7.2.–7.4 (3H), 7.6–7.9 (4H), 8.4 (2H) and 9.6 (1H) ppm.

Example 6

2-(Pyrazin-2-yl)benzimidazole-4-carboxamide

A solution of 1.68 g (7.5 mmol) of 2,3-diaminobenzamide and 3.04 g (30 mmol) of triethylamine in 50 ml of dimethylformamide was stirred at room temperature for 1 hour. 0.93 g (7.5 mmol) of pyrazine-2-carboxylic acid and 1.01 g (7.5 mmol) of N-hydroxybenzotriazole (HOBt) were added. After stirring at room temp. for 15 minutes, the mixture was cooled to 0° C. 1.44 g (7.5 mmol) of N'-(3-dimethylaminopropyl)-N-ethylcarbodiimide (EDC) were added, and the mixture was stirred at room temp. for 16 hours. The reaction mixture was then concentrated in vacuo. The residue was partitioned between methylene chloride and saturated sodium bicarbonate solution. The aqueous phase was extracted with methylene chloride. The combined organic phases were dried over magnesium sulfate. The residue obtained after concentration in vacuo was taken up in 50 ml of glacial acetic acid and refluxed for 30 minutes. The reaction mixture was concentrated in vacuo, and the residue was stirred in diethyl ether. The precipitate was removed by filtration and dried at 40° C. in vacuo. 1.11 g of brown crystals were obtained.

1H-NMR (D$_6$-DMSO): δ=7.42 (1H), 7.6–7.9 (2H), 7.95 (1H), 8.8–8.9 (2H), 9.2 (1H), 9.7 (1H) ppm. MS: m/e=239 (M$^+$).

Examples 7–11 were prepared in analogy to Example 6:

Example 7

2-(Quinolin-6-yl)benzimidazole-4-carboxamide

1H-NMR (D$_6$-DMSO): δ=7.4 (1H), 7.55–8.2 (4H), 8.2–8.3 (1H), 8.4–8.7 (2H), 8.8–9.2 (2H), 9.3 (broad, 1H), 13.0 (broad, 1H) ppm. MS: m/e=288 (M$^+$).

Example 8

2-(1-(2-(N,N-Diethylamino)eth-1-yl)pyrrol-3-yl)benzimidazole-4-carboxamide

1H-NMR (D$_6$-DMSO): δ=0.8–1.0 (6H), 2.4–2.6 (4H), 2.7–2.8 (2H), 4.0–4.1 (2H), 6.7–6.75 (1H), 7.1–7.15 (1H), 7.5–7.8 (3H), 8.0–8.2 (2H) ppm. MS: m/e=326 (M$^+$+H).

Example 9

2-(1-(N,N-Dimethylamino)naphthalen-4-yl)benzimidazole-4-carboxamide×HCl

1H-NMR (D$_6$-DMSO): δ=2.9 (3H), 3.0 (3H), 7.25–7.3 (1H), 7.4–7.7 (2H), 7.75 (1H), 7.8 (1H), 7.8–7.9 (2H), 8.2–8.3 (2H) ppm. MS: m/e=330 (M$^+$).

Example 10

2-Pyridin-3-ylbenzimidazole-4-carboxamide

1H-NMR (D$_6$-DMSO): δ=7.25 (1H), 7.5–7.7 (3H), 7.75 (1H), 7.8–8.0 (2H), 7.25–7.3 (1H), 7.4 (1H) ppm. MS: m/e=238 (M$^+$).

Example 11

2-(2-Aminomethylthiazol-4-yl)benzimidazole-4-carboxamide×HCl

1H-NMR (D$_6$-DMSO): δ=4.0–5.0 (broad, NH), 4.75 (1H), 4.8 (1H), 7.5 (1H), 7.8 (1H), 7.95 (1H), 9.0 (broad) ppm. MS: m/e=273 (M$^+$).

Example 12

2-Isoxazol-5-ylbenzimidazole-4-carboxamide

A solution of 0.81 g (7.5 mmol) of ethyl chloroformate in 5 ml of tetrahydrofuran was added dropwise to a solution of 0.85 g (7.5 mmol) of isoxazole-5-carboxylic acid and 3.79 g (37.5 mmol) of triethylamine in 50 ml of tetrahydrofuran at −10° C. After stirring at −10° C. for 1 hour, 1.68 g (7.5 mmol) of 2,3-diaminobenzamide were added. The reaction mixture was stirred at room temp. for 16 hours. The reaction mixture was then concentrated in vacuo. The residue was partitioned between methylene chloride and saturated sodium bicarbonate solution. The aqueous phase was extracted with methylene chloride. The combined organic phases were dried over magnesium sulfate. The residue obtained after concentration in vacuo was taken up in 10 ml of glacial acetic acid and stirred at 100° C. for 60 minutes. The reaction mixture was concentrated in vacuo, and the residue was partitioned between ethyl acetate and saturated sodium bicarbonate solution. The organic phase was dried over magnesium sulfate and concentrated in vacuo. The residue was taken up in isopropanol, and the precipitate produced with petroleum ether was filtered off, washed with petroleum ether and dried in vacuo at 35° C. 120 mg of yellow crystals were obtained.

1H-NMR ($D_6$-DMSO): δ=7.3 (1H), 7.45–7.5 (1H), 7.75–8.0 (3H), 8.8 (1H), 9.1 (1H) ppm. MS: m/e=228 ($M^+$).

Example 13

2-(2-(2-(N,N-Diethylamino)eth-1-ylamino)pyridin-3-yl)benzimidazole-4-carboxamide×2HCl a) Ethyl 2-(2-(N,N-diethylamino)eth-1-ylamino)nicotinate×2 oxalic Acid A mixture of 1.86 g (0.01 mol) of ethyl 2-chloronicotinate, 1.16 g (0.01 mol) of 1-(N,N-diethylamino)-2-aminoethane, 2.76 g (0.02 mol) of potassium carbonate and a spatula tip of 18-crown-6 in 50 ml of dimethylformamide was stirred at 120° C. for 6 hours. After removal of the solids, the reaction mixture was concentrated in vacuo. The residue was taken up in ethyl acetate. The organic phase was washed with water, dried over magnesium sulfate and concentrated in vacuo. The pale brown oil was taken up in isopropanol, and the oxalate was precipitated with oxalic acid. 2.2 g of white crystals were obtained after removal and drying in vacuo.

b) 2-(2-(N,N-Diethylamino)eth-1-ylamino)nicotinic Acid 1.15 g (4.33 mmol) of the free base of the product 13a were introduced into 100 ml of methanol, and 100 ml of 2M sodium hydroxide solution were added. The reaction mixture was stirred at room temp. for 16 hours. The reaction mixture was concentrated in vacuo, and 100 ml of 2M hydrochloric acid were added to the aqueous residue. Concentration in vacuo resulted in 12.47 g of a mixture of product and NaCl.

c) 2-(2-(2-(N,N-Diethylamino)eth-1-ylamino)pyridin-3-yl)benzimidazole-4-carboxamide×2HCl 0.84 g (3.75 mmol) of 2,3-diaminobenzamide was stirred in 35 ml of pyridine for 5 minutes, and then 0.89 g (3.75 mmol) of product 13b was added. The reaction mixture was stirred for 5 minutes and cooled to 0° C. After addition of 0.72 g (3.75 mmol) of N'-(3-dimethylaminopropyl)-N-ethylcarbodiimide (EDC), the reaction mixture was stirred at 0° C. for 1 hour and then at room temp. for 16 hours. The reaction mixture was concentrated in vacuo and then concentrated twice with toluene in vacuo. The residue was partitioned between water and ethyl acetate. The aqueous phase was basified with 1M sodium hydroxide solution, saturated with solid sodium chloride and exhaustively extracted with methylene chloride. The organic phase was dried with magnesium sulfate and concentrated in vacuo. The residue was taken up in 2 ml of glacial acetic acid and stirred at 100° C. for 1 hour. The residue after concentration in vacuo was dissolved in methylene chloride, and the hydrochloride was precipitated with ethereal hydrochloric acid solution and was removed by filtration, washed with diethyl ether and dried in vacuo at 35° C. 0.52 g of a yellow powder was obtained.

1H-NMR ($D_6$-DMSO): δ=1.1–1.3 (6H), 3.1–3.3 (4H), 3.35–3.5 (2H), 4.0–4.15 (2H), 7.0–7.1 (1H), 7.4–7.5 (1H), 7.8–7.95 (2H), 8.2–8.3 (1H), 8.4 (1H), 8.7 (1H), 10.6 (1H) ppm. MS: m/e=353 ($M^++H$).

Example 14

2-(2-((2-(N,N-Diethylamino)eth-1-yl)methylamino)pyridin-3-yl)benzimidazole-4-carboxamide×2HCl Synthesis took place in analogy to Example 13.

1H-NMR ($D_6$-DMSO): δ=1.25 (6H), 2.6 (3H), 3.1–3.25 (4H), 3.3–3.45 (2H), 3.8–3.9 (2H), 7.0–7.1 (1H), 7.45–7.55 (1H), 7.8 (1H), 7.95–8.05 (2H), 8.15–8.2 (1H), 8.4–8.45 (1H), 8.8 (broad, 1H), 10.55 (broad, 1H) ppm. MS: m/e=367 ($M^++H$).

Example 15

2-(6-((2-(N,N-Diethylamino)eth-1-yl)methylamino)pyridin-3-yl)benzimidazole-4-carboxamide×2 HCl Synthesis took place in analogy to Example 13.

1H-NMR ($D_4$-Methanol): δ=1.45 (6H), 3.25 (3H), 3.3–3.5 (6H), 4.2 (2H), 7.1 (1H), 7.7 (1H), 7.95 (1H), 8.05 (1H), 8.35 (1H), 8.7 (1H) ppm. MS: m/e=367 ($M^++H$).

Example 16

2-(6-(4-Propylpiperazin-1-yl)pyridin-3-yl)benzimidazole-4-carboxamide

Synthesis took place in analogy to Example 13.

1H-NMR ($D_6$-DMSO): δ=0.95 (3H), 1.7–1.8 (2H), 2.7–2.8 (2H), 3.0–3.2 (6H), 4.5–4.65 (2H), 7.15–7.25 (1H), 7.4 (1H), 7.75–7.95 (2H), 8.45 (1H), 9.05 (1H), 10.95 (broad, 1H) ppm. MS: m/e=365 ($M^++H$).

Example 17

2-(2-(3-(N,N-Diethylamino)prop-1-ylamino)pyridin-3-yl)benzimidazole-4-carboxamide×2 HCl Synthesis took place in analogy to Example 13.

1H-NMR ($D_4$-Methanol): δ=1.2 (6H), 2.0–2.1 (2H), 2.85–3.0 (6H), 3.6–3.7 (2H), 7.7–7.8 (1H), 7.3–7.4 (1H), 8.1–8.2 (2H), 7.75 (1H), 7.9 (1H) ppm. MS: m/e=367 ($M^++H$).

Example 18

2-(3-Aminothiophen-4-yl)benzimidazole-4-carboxamide×HCl a) 4-tert-Butyloxycarbonylaminothiophene-3-carboxylic Acid 2.76 g (0.022 mol) of ethyl 4-aminothiophene-3-carboxylate and 4.81 g (0.022 mol) of di-tert-butyl dicarbonate were stirred with a spatula tip of 4-N,N-dimethylaminopyridine in 100 ml of tetrahydrofuran at room temp. for 8 hours. The reaction mixture was diluted with ethyl acetate and washed three times with 5% citric acid solution. The organic phase was dried over magnesium sulfate and then concentrated in vacuo. The residue was dissolved in 100 ml of ethanol and, after addition of 100 ml of 2M sodium hydroxide solution, the mixture was stirred at room temp. for 16 hours. The aqueous residue after concentration in vacuo was mixed with 100 ml of 2M hydrochloric acid. The precipitate was removed by filtration and washed with water, and dried at 40° C. in vacuo. The residue was filtered with ethyl acetate. After filtration, the filtrate was concentrated in vacuo. 0.85 g of yellow powder was obtained.

b) 2-(3-Aminothiophen-4-yl)benzimidazole-4-carboxamide×HCl

A solution of 0.35 g (3.21 mmol) of ethyl chloroformate in 5 ml of methylene chloride was added dropwise to a solution of 0.78 g (3.21 mmol) of product 18a and 1.67 g (16.05 mmol) of triethylamine in 25 ml of methylene chloride at −10° C. After stirring at −10° C. for 1 hour, 0.72 g (3.21 mmol) of 2,3-diaminobenzamide was added. The reaction mixture was stirred at room temp. for 16 hours. The reaction mixture was then concentrated in vacuo. The residue was partitioned between methylene chloride and saturated sodium bicarbonate solution. The aqueous phase was extracted with methylene chloride. The combined organic phases were dried over magnesium sulfate. The residue obtained after concentration in vacuo was taken up in 10 ml of glacial acetic acid and stirred at 100° C. for 30 minutes. The reaction mixture was concentrated in vacuo, and the residue was taken up in a little ethyl acetate. The precipitate produced with n-pentane was filtered off and taken up in 5 ml of methylene chloride. After addition of 5 ml of 4M dioxane HCl solution, the mixture was stirred at room temp. for 16 hours. The crystals were filtered off, washed with methylene chloride and diethyl ether and dried in vacuo at 35° C. 30 mg of ocher-colored crystals were obtained.

1H-NMR ($D_6$-DMSO): δ=7.3–7.4 (1H), 7.7–7.8 (2H), 7.85–7.9 (1H), 8.6 (1H), 8.75 (1H) ppm.

MS: m/e=258 ($M^+$).

Example 19

2-(2-(2-(N,N-Diethylamino)eth-1-yloxy)pyridin-3-yl)benzimidazole-4-carboxamide×HCl a) Ethyl 2-(2-(N,N-diethylamino)eth-1-yloxy)nicotinate×2 Oxalic Acid 1.05 g (6.28 mmol) of ethyl 2-hydroxynicotinate, 1.64 g (6.28 mmol) of 2-bromo-N,N-diethylethylamine×HBr, 1.74 g of potassium carbonate and a spatula tip of 18-crown-6 in 25 ml of dimethylformamide were stirred at room temp. for 16 hours. The solids were then removed, and the filtrate was concentrated in vacuo. The residue was partitioned between water and ethyl acetate. The organic phase was dried over magnesium sulfate and concentrated in vacuo. The residue was taken up in isopropanol, and the oxalate was precipitated with oxalic acid and, after removal, was dried at 40° C. in vacuo. 2.2 g of white crystals were obtained.

b) 2-(2-(N,N-Diethylamino)eth-1-yloxy)nicotinic Acid 0.87 g (3.27 mmol) of product 21a was reacted in analogy to Example 13b. 3.54 g of a mixture of product 18b and NaCl were obtained.

c) 2-(2-(2-(N,N-Diethylamino)eth-1-yloxy)pyridin-3-yl)benzimidazole-4-carboxamide×HCl 1.68 g (7.5 mmol) of 2,3-diaminobenzamide and 1.79 g (7.5 mmol) of product 21b were reacted in analogy to Example 13c. 390 mg of an ocher-colored powder were obtained.

1H-NMR ($D_6$-DMSO): δ=1.2–1.3 (6H), 3.2–3.3 (4H), 3.4–3.5 (2H), 4.5–4.6 (2H), 6.7–6.8 (1H), 7.4–7.5 (1H), 7.8 (1H), 7.9–8.1 (2H), 8.3–8.4 (1H), 8.7 (broad, 1H), 8.9–9.0 (1H), 10.8 (broad, 1H) ppm.

MS: m/e=353 ($M^+$).

Example 20

2-(1-Phenylsulfonylpyrrol-3-yl)benzimidazole-4-carboxamide a) 1-Phenylsulfonylpyrrole-3-carbaldehyde A solution of 5.91 g (0.037 mol) of 2,5-dimethoxytetrahydrofuran-3-carbaldehyde, 5.80 g (0.037 mol) of phenylsulfonamide and a spatula tip of 4-toluenesulfonic acid in 50 ml of toluene was refluxed with a water trap until water no longer separated out. The reaction mixture was washed three times with water. The organic phase was dried over magnesium sulfate with addition of activated carbon and silica gel and concentrated in vacuo. 7.68 g of a brown resin were obtained.

b) 2-(1-Phenylsulfonylpyrrol-3-yl)benzimidazole-4-carboxamide 1.68 g (7.5 mmol) of 2,3-diaminobenzamide were added to a solution of 0.84 g (15 mmol) of potassium hydroxide powder in 100 ml of ethanol. After stirring for 5 minutes, 1.35 g (22.5 mmol) of glacial acetic acid were rapidly added dropwise, and a solution of product 20a in 20 ml of ethanol was added dropwise over the course of 30 minutes. A warm solution of 2.49 g (12.5 mmol) of copper(II) acetate in 20 ml of water was then rapidly added dropwise. The reaction mixture was refluxed for 2 hours. Solids were then removed by filtration. The residue was partitioned between methylene chloride and water. The mixture was made alkaline with aqueous ammonia. The aqueous phase was extracted with methylene chloride. The combined organic phases were dried over magnesium sulfate and concentrated in vacuo. 0.82 g of yellow crystals were obtained.

1H-NMR ($D_6$-DMSO): δ=7.05 (1H), 7.3–7.35 (1H), 7.55–7.65 (2H), 7.65–7.75 (5H), 7.8–7.9 (2H), 8.0–8.1 (2H), 8.2 (1H), 9.3 (1H) ppm. MS: m/e=366 ($M^+$).

Example 21

2-Pyrrol-3-ylbenzimidazole-4-carboxamide

A mixture of 0.5 g (1.36 mmol) of product 20b and 0.75 g of potassium carbonate in 25 ml of methanol and 10 ml of water was refluxed for 2 hours. The reaction mixture was then concentrated in vacuo. The residue was diluted with saturated sodium bicarbonate solution and extracted several times with ethyl acetate. Drying over magnesium sulfate was followed by concentration in vacuo. The residue was dissolved in a little ethyl acetate/tetrahydrofuran, and the product was precipitated with n-pentane and was isolated by filtration and dried in vacuo at 30° C. 80 mg of yellow crystals were obtained.

1H-NMR ($D_6$-DMSO): δ=6.75 (1H), 6.9 (1H), 7.2–7.3 (1H), 7.5–7.7 (2H), 7.7–7.8 (2H), 9.4 (broad, 1H), 11.3 (broad, 1H) ppm. 20 MS: m/e=226 ($M^++H$).

Example 22

2-(2-Methylimidazo[1,5-a]pyridin-8-yl)benzimidazole-4-carboxamide

Synthesis took place in analogy to Example 20b.

1H-NMR ($D_6$-DMSO): δ=2.7 (3H), 5.8 (broad, NH), 7.0–7.4 (5H), 8.4 (1H), 8.55 (1H), 10.9 (1H) ppm. MS: m/e=291 ($M^+$).

Example 23

2-(Pyrazol-4-yl)benzimidazole-4-carboxamide 35 0.56 g (5 mmol) of 4-pyrazolecarboxylic acid was stirred with 0.81 g (5 mmol) of carbonyldiimidazole in 20 ml of dimethylformamide at room temp. for 2 hours. 1.12 g (5 mmol) of 2,3-diaminobenzamide in 10 ml of pyridine were added. The reaction mixture was stirred at 50° C. for 2 hours. The reaction mixture was then concentrated in vacuo, and the residue was stirred with water. The precipitate was filtered off and dried in vacuo at 40° C. and then stirred in 10 ml of glacial acetic acid at 100° C. The residue after concentration in vacuo was stirred with saturated sodium bicarbonate solution. After filtration, the filtrate was concentrated with toluene in vacuo several times. The residue was stirred with tetrohydrofuran. Concentration in vacuo resulted in 150 mg of yellow powder.

1H-NMR ($D_6$-DMSO): δ=7.2 (1H), 7.55–7.7 (3H), 7.75 (1H), 8.4 (2H), 9.3 (broad, 1H) ppm. MS: m/e=291 ($M^+$).

Example 24

2-(2-(3-(N,N-Diethylamino)prop-1-ylamino)pyridin-4-yl)benzimidazole-4-carboxamide a) tert-Butyl 2-(3-(N,N-diethylamino)prop-1-ylamino)-isonicotinate 1.02 g (4.77 mmol) of tert-butyl 2-chloroisonicotinate, 5 ml of 3-diethylamino-1-propylamine, 0.66 g (4.77 mmol) of potassium carbonate, a spatula tip of Cu powder and a spatula tip of 18-crown-6 were refluxed for 4 hours. Flash chromatography of the reaction mixture (toluene/tetrahydrofuran/methanol, 4/1/1+2.5% triethylamine) resulted in 0.69 g of pale brown oil.

b) 2-(3-(N,N-Diethylamino)prop-1-ylamino)isonicotinic Acid×HCl

A solution of 0.5 g (1.63 mmol) of product 24a in 7.5 ml of dioxane and 7.5 ml of 2M hydrochloric acid was stirred at 100° C. for 1 hours. Concentration of the reaction mixture in vacuo and drying of the residue in vacuo at 50° C. resulted in 0.43 g of beige crystals.

c) 2-(2-(3-(N,N-Diethylamino)prop-1-ylamino)pyridin-4-yl)benzimidazole-4-carboxamide 0.36 g (1.25 mmol) of product 24b was introduced into 10 ml of a mixture of dimethylformamide and pyridine (1:1) and stirred for 15 minutes. After addition of 0.21 g (1.31 mmol) of carbonyldiimidazole, the reaction mixture was stirred at room temp. for 1 hour. A solution of 0.28 g (1.25 mmol) of 2,3-diaminobenzamide in 5 ml of dimethylformamide/pyridine was then added. The reaction mixture was stirred at 50° C. for 2 hours. The residue after concentration of the reaction mixture in vacuo was partitioned between ethyl acetate and saturated sodium bicarbonate solution. The organic phase was separated off, dried over magnesium sulfate and concentrated in vacuo. The residue was stirred in 20 ml of glacial acetic acid at 100° C. for 1 hour. The residue after concentration of the reaction mixture in vacuo was purified by flash chromatography (toluene/tetrahydrofuran/methanol, 4/1/1+2.5% triethylamine). The product obtained in this way was dissolved in a little acetone. The precipitate obtained with diethyl ether was separated off and dried at 40° C. in vacuo. 0.22 g of yellow powder was obtained.

1H-NMR ($D_6$-DMSO): δ=1.15–1.25 (6H), 1.9–2.05 (2H), 3.0–3.2 (8H), 7.1 (1H), 7.3–7.35 (2H), 7.8 (1H), 7.9 (1H), 7.95 (1H), 8.2 (1H), 9.3 (1H), 14.0 (1H) ppm. MS: m/e=366 ($M^+$).

Example 25

2-(2-((2-(N,N-Diethylamino)eth-1-yl)methylamino)pyridin-4-yl)benzimidazole-4-carboxamide×½ Fumaric Acid Synthesis took place in analogy to Example 24.

1H-NMR ($D_6$-DMSO): δ=1.2–1.35 (6H), 3.2 (3H), 3.2–3.5 (4H), 3.95–4.05 (4H), 6.65 (2H), 7.4 (1H), 7.5 (2H), 7.6 (1H), 7.75–7.85 (2H), 7.9 (1H), 8.3 (1H), 9.25 (1H), 14.0 (1H) ppm. MS: m/e=366 ($M^+$).

Example 26

2-(2-(2-(N,N-Diethylamino)eth-1-ylamino)pyridin-4-yl)benzimidazole-4-carboxamide×2 HCl Synthesis took place in analogy to Example 24.

1H-NMR ($D_6$-DMSO): δ=1.0–1.05 (6H), 3.3–3.45 (4H), 3.9–4.1 (4H), 6.65 (1H), 7.25–7.4 (2H), 7.5 (1H), 7.55–7.65 (2H), 7.75 (1H), 7.85 (1H), 7.9–8.0 (1H), 8.05 (1H), 8.1–8.25 (2H), 9.0 (1H), 10.55 (broad, 1H) ppm. MS: m/e=353 ($M^+$+H).

Example 27

2-(2-(2-(Pyrrolidin-1-yl)eth-1-ylamino)pyridin-4-yl)benzimidazole-4-carboxamide

Synthesis took place in analogy to Example 24.

1H-NMR ($D_6$-DMSO): δ=1.7–1.8 (4H), 2.55–2.7 (4H), 2.75 (2H), 3.5 (2H), 6.9 (1H), 7.25 (1H), 7.3–7.45 (2H), 7.75 (1H), 7.85–7.95 (2H), 8.15 (1H), 9.25 (1H) ppm. MS: m/e=351 ($M^+$).

Example 28

2-(2-(3-(4-Methylpiperazin-1-yl)prop-1-ylamino)pyridin-4-yl)benzimidazole-4-carboxamide×2 Fumaric Acid Synthesis took place in analogy to Example 24.

1H-NMR ($D_6$-DMSO): δ=2.7–2.85 (2H), 2.45–2.8 (13H), 3.25–3.4 (2H), 6.6 (4H), 6.95 (broad, 1H), 7.25 (1H), 7.3 (1H), 7.4 (1H), 7.8 (1H), 7.85–7.95 (2H), 8.15 (1H), 9.25 (broad, 1H), 13.8 (broad, 1H) ppm. MS: m/e=394 ($M^+$+H).

Example 29

2-(6-(2-(Pyrrolidin-1-yl)eth-1-ylamino)pyridin-2-yl)benzimidazole-4-carboxamide

Synthesis took place in analogy to Example 24.

1H-NMR ($D_6$-DMSO): δ=1.65–1.8 (4H), 2.5–2.6 (4H), 2.65–2.75 (2H), 3.55–3.7 (2H), 6.65–6.75 (2H), 7.35 (1H), 7.5–7.6 (2H), 7.75–7.85 (2H), 7.9 (1H), 9.3 (broad, 1H) ppm. MS: m/e=351 ($M^+$+H).

Example 30

2-(6-(3-(N,N-Diethylamino)prop-1-ylamino)pyridin-2-yl)benzimidazole-4-carboxamide Synthesis took place in analogy to Example 24.

1H-NMR ($D_6$-DMSO): δ=MS: m/e=367 ($M^+$+H).

Example 31

2-(6-(2-(N,N-Diethylamino)eth-1-ylamino)pyridin-2-yl)benzimidazole-4-carboxamide×½ Fumaric Acid Synthesis took place in analogy to Example 24.

1H-NMR ($D_6$-DMSO): δ=0.95–1.1 (6H), 2.65–2.8 (6H), 3.55–3.7 (2H), 6.55 (1H), 6.7 (1H), 7.3 (1H), 7.5–7.6 (2H), 7.7–7.8 (2H), 7.9 (1H), 9.3 (broad, 1H) ppm. MS: m/e=353 ($M^+$+H).

Example 32

2-(6-(3-(4-Methylpiperazin-1-yl)prop-1-ylamino)
pyridin-2-yl)benzimidazole-4-carboxamide Synthesis took place in analogy to Example 24.
MS: m/e=394 (M$^+$+H).

Example 33

2-(6-(2-((N,N-Diethylamino)eth-1-yl)methylamino)
pyridin-2-yl)benzimidazole-4-carboxamide×3
Fumaric Acid Synthesis took place in analogy to Example 24.
1H-NMR (D$_6$-DMSO): δ=1.05–1.2 (6H), 3.0–3.1 (6H), 3.15 (3H), 4.0–4.15 (2H), 6.6 (6H), 6.75–6.85 (2H), 7.05 (broad, 1H), 7.35 (1H), 7.65–7.8 (4H), 7.9 (1H), 8.2 (broad, 1H), 9.3 (broad, 1H) ppm. MS: m/e=367 (M$^+$+H).

Example 34

2-(2-(4-Phenylpiperazin-1-yl)pyridin-5-yl)
benzimidazole-4-carboxamide×2 HCl a) Ethyl 6-(4-phenylpiperazin-1-yl)nicotinate A mixture of 3.72 g (0.02 mol) of ethyl 6-chloronicotinate and 6.44 g (0.04 mol) of N-phenylpiperazine was stirred at 100° C. for 1 hour. The reaction mixture was concentrated in vacuo. The residue was stirred with isopropanol. 7.8 g of a yellow solid were obtained.

b) 6-(4-Phenylpiperazin-1-yl)nicotinic Acid 2.8 g of product 34b were obtained in analogy to Example 13b.

c) 2-(2-(4-Phenylpiperazin-1-yl)pyridin-5-yl)benzimidazole-4-carboxamide 2.27 g (0.008 mol) of product 34b and 1.79 g (0.008 mol) of 2,3-diaminobenzamide were reacted in analogy to Example 24c. 0.25 g of a brown solid was obtained.
1H-NMR (D$_4$-Methanol): δ=3.85–3.95 (4H), 4.35–4.45 (4H), 7.35 (1H), 7.55–7.7 (4H), 7.75–7.85 (2H), 7.95 (1H), 8.05 (1H), 8.2 (1H), 9.05 (1H) ppm. MS: m/e=399 (M$^+$+H).

Example 35

2-(2-(4-Benzylpiperazin-1-yl)pyridin-5-yl)
benzimidazole-4-carboxamide×2 HCl

Synthesis took place in analogy to Example 34.
1H-NMR (D$_6$-DMSO): δ=3.0–3.2 (2H), 3.3–3.45 (2H), 3.5–3.6 (2H), 4.4 (2H), 4.55–4.7 (2H), 7.2 (1H), 7.4–7.5 (4H), 7.7 (2H), 7.75 (1H), 7.8 (1H), 7.85 (1H), 8.5 (1H), 8.8 (broad, 1H), 9.1 (1H), 10.4 (broad, 1H) ppm. MS: m/e=412 (M$^+$).

Example 36

2-(2-(4-tert-Butylpiperazin-1-yl)pyridin-5-yl)
benzimidazole-4-carboxamide

Synthesis took place in analogy to Example 34.
1H-NMR (D$_6$-DMSO): δ=1.4 (9H), 3.0–3.2 (2H), 3.45–3.7 (4H), 4.5–4.7 (2H), 7.15 (1H), 7.3 (1H), 7.7–7.75 (2H), 7.8 (1H), 8.45 (1H), 9.05 (1H), 9.3 (1H), 10.7 (broad, 1H) ppm. MS: m/e=379 (M$^+$+H).

Example 37

2-(2-(4-n-Butylpiperazin-1-yl)pyridin-5-yl)
benzimidazole-4-carboxamide×HCl

Synthesis took place in analogy to Example 34.
1H-NMR (D$_6$-DMSO): δ=0.9–1.0 (3H), 1.35 (2H), 1.75 (2H), 3.0–3.2 (4H), 3.5–3.7 (4H), 4.5–4.7 (2H), 7.25 (1H), 7.55 (1H), 7.8–8.0 (3H), 8.5–8.7 (2H), 9.15 (1H), 11.4 (broad, 1H) ppm. MS: m/e=378 (M$^+$).

Example 38

2-(2-(Piperidin-1-yl)pyridin-5-yl)benzimidazole-4-carboxamide

Synthesis took place in analogy to Example 34.
MS: m/e=322 (M$^+$+H).

Example 39

2-(2-(Pyrrolidin-1-yl)pyridin-5-yl)benzimidazole-4-carboxamide

Synthesis took place in analogy to Example 34.
MS: m/e=308 (M$^+$+H).

Example 40

2-(2-(2-(Pyrrolidin-1-yl)eth-1-ylamino)pyridin-5-yl)
benzimidazole-4-carboxamide Synthesis took place in analogy to Example 34.
MS: m/e=351 (M$^+$+H).

Example 41

2-(2-(Piperazin-1-yl)pyridin-5-yl)benzimidazole-4-carboxamide

Synthesis took place in analogy to Example 34.
MS: m/e=323 (M$^+$+H).

Example 42

2-(2-(4-Methylpiperazin-1-yl)pyridin-5-yl)
benzimidazole-4-carboxamide

Synthesis took place in analogy to Example 34.
MS: m/e=337 (M$^+$+H).

Example 43

2-(2-(4-Ethylpiperazin-1-yl)pyridin-5-yl)
benzimidazole-4-carboxamide

Synthesis took place in analogy to Example 34.
MS: m/e=351 (M$^+$+H).

Example 44

2-(2-(2-(Piperidin-1-yl)eth-1-ylamino)pyridin-5-yl)
benzimidazole-4-carboxamide

Synthesis took place in analogy to Example 34.
MS: m/e=365 (M$^+$+H).

Example 45

2-(2-(3-(N,N-Dimethylamino)prop-1-ylamino)
pyridin-5-yl)benzimidazole-4-carboxamide Synthesis took place in analogy to Example 34.
MS: m/e=367 (M$^+$+H).

Example 46

2-(2-(3-(4-Methylpiperazin-1-yl)prop-1-ylamino)
pyridin-5-yl)benzimidazole-4-carboxamide Synthesis took place in analogy to Example 34.
MS: m/e=394 (M$^+$+H).

Example 47

2-(2-(2-(N,N-Diethylamino)eth-1-ylamino)pyridin-5-yl)benzimidazole-4-carboxamide

Synthesis took place in analogy to Example 34.
MS: m/e=353 (M$^+$+H).

Example 48

2-(6-(2-(N,N-Diethylamino)eth-1-yloxy)pyridin-2-yl)benzimidazole-4-carboxamide×Fumaric Acid a) tert-Butyl 6-(2-(N,N-diethylamino)eth-1-yloxy)picolinate 1.03 g of diethylaminoethanol were introduced into 25 ml of dimethylformamide. At room temp., 0.22 g (9.26 mmol) of sodium hydride (60% suspension in white oil) was added. After stirring at room temp. for 30 minutes, a solution of 2.03 g (8.882 mmol) of tert-butyl 6-bromopicolinate in 20 ml of dimethylformamide was added dropwise. The reaction mixture was stirred at room temp. for 16 hours. After decomposition of excess sodium hydride with water, the reaction mixture was concentrated in vacuo. The residue was purified by flash chromatography (toluene/tetrahydrofuran/methanol, 4/1/1+2.5% triethylamine). 0.67 g of a pale brown oil was obtained.

b) A solution of 0.55 g (2.07 mmol) of product 42a in 7.5 ml of dioxane and 7.5 ml of 2M hydrochloric acid was stirred at 100° C. for 3 hours. Concentration of the reaction mixture in vacuo and drying the residue in vacuo at 50° C. resulted in 0.58 g of a yellow resin.

c) 2-(6-(2-(N,N-Diethylamino)eth-1-yloxy)pyridin-2-yl)benzimidazole-4-carboxamide×Fumaric Acid 0.49 g (1.78 mmol) of product 42b and 0.40 g (1.78 mmol) of 2,3-diaminobenzamide were reacted in analogy to Example 24c. The residue was taken up in isopropanol, and the fumarate was precipitated with fumaric acid. 40 mg of a yellow powder were obtained.

1H-NMR (D$_6$-DMSO): δ=1.1–1.3 (6H), 3.1–3.25 (4H), 3.4–3.5 (2H), 4.85–5.0 (2H), 7.05 (1H), 7.4 (1H), 7.8–8.0 (4H), 8.1 (1H), 9.3 (broad, 1H), 13.5 (broad, 1H) ppm. MS: m/e=354 (M$^+$+H).

Example 49

2-(6-(2-(Piperidin-1-yl)eth-1-yloxy)pyridin-2-yl)benzimidazole-4-carboxamide a) Ethyl 6-(2-(Piperidin-1-yl)eth-1-yloxy)picolinate×HCl

A mixture of 1.50 g (9 mmol) of ethyl 6-hydroxypicolinate, 1.33 g (9 mmol) of 2-chloroethylpiperidine, 2.49 g (18 mmol) of potassium carbonate and a spatula tip of 18-crown-6 in 25 ml of dimethylformamide was stirred at 120° C. for 6 hours. After removal of the solids, the reaction mixture was concentrated in vacuo. The residue was taken up in ethyl acetate, and 1M ethereal hydrochloric acid solution was added to turbidity. The hydrochloride was precipitated with diethyl ether. After filtration and washing with tetrahydrofuran, the residue was dried at 35° C. in vacuo. 1.97 g of white crystals were obtained.

b) 6-(2-(Piperidin-1-yl)eth-1-yloxy)picolinic Acid 1.77 g (5.62 mmol) of product 43a were stirred in 25 ml of ethanol with 25 ml of 2M sodium hydroxide solution at room temp. overnight. The reaction mixture was mixed with 25 ml of 2M hydrochloric acid and then concentrated in vacuo. The residue was extracted with dimethylformamide, and the filtrate was concentrated in vacuo. The residue was taken up in a little ethanol, and the product was precipitated with diethyl ether. 1.13 g of a beige powder were obtained.

c) 2-(6-(2-(Piperidin-1-yl)eth-1-yloxy)pyridin-2-yl)benzimidazole-4-carboxamide×½ fumaric Acid 1.08 g (4.31 mmol) of product 43b and 0.97 g (4.31 mmol) of 2,3-diaminobenzamide were reacted in analogy to Example 24c. Purification took place by flash chromatography (toluene/tetrahydrofuran/methanol, 4/1/1+2.5% triethylamine). The crude product obtained in this way was taken up in isopropanol, and the hemifumarate was precipitated with fumaric acid. 0.71 g of beige crystals was obtained.

1H-NMR (D$_6$-DMSO): δ=1.35–1.45 (2H), 1.45–1.6 (4H), 1.55–1.75 (4H), 1.85–1.95 (2H), 4.6–4.75 (2H), 6.6 (1H), 7.0 (1H), 7.4 (1H), 7.8–7.95 (4H), 8.05 (1H), 9.3 (1H) ppm. MS: m/e=366 (M$^+$+H).

Example 50

2-(6-(3-(N-Benzyl-N-methylamino)prop-1-yloxy)pyridin-2-yl)benzimidazole-4-carboxamide

Synthesis took place in analogy to Example 49.
1H-NMR (D$_6$-DMSO): δ=2.3–2.4 (2H), 2.7 (3H), 4.3–4.5 (4H), 4.6–4.7 (2H), 7.0 (1H), 7.35–7.45 (4H), 7.55–7.65 (2H), 7.8–8.0 (4H), 8.1–8.15 (1H), 9.1 (1H), 11.0 (1H) ppm. MS: m/e=416 (M$^+$+H).

Example 51

2-(6-(3-(N,N-Diethylamino)prop-1-yloxy)pyridin-2-yl)benzimidazole-4-carboxamide

Synthesis took place in analogy to Example 49.
1H-NMR (D$_6$-DMSO): δ=1.2–1.3 (6H), 2.15–2.25 (2H), 3.1–3.4 (6H), 25 4.6–4.7 (2H), 7.0 (1H), 7.4 (1H), 7.8–8.0 (4H), 8.1 (1H), 9.2 (1H), 10.0 (broad, 1H) ppm. MS: m/e=368 (M$^+$+H).

Example 52

2-(6-(3-(4-Methylpiperazin-1-yl)prop-1-yloxy)pyridin-2-yl)benzimidazole-4-carboxamide×2 Fumaric Acid

Synthesis took place in analogy to Example 49.
1H-NMR (D$_6$-DMSO): δ=1.9–2.0 (2H), 2.25 (3H), 3.3–3.6 (10H), 4.5–4.6 (2H), 6.6 (4H), 7.0 (1H), 7.45 (1H), 7.8 (1H), 7.9–7.95 (2H), 8.0 (1H), 9.3 (1H) ppm. MS: m/e=395 (M$^+$+H).

Example 53

2-(2-(3-(N,N-Diethylamino)prop-1-yloxy)pyridin-5-yl)benzimidazole-4-carboxamide×HCl

Synthesis took place in analogy to Example 49.
1H-NMR (D$_6$-DMSO): δ=1.2–1.3 (6H), 2.1–2.25 (2H), 3.1–3.25 (6H), 4.4–4.5 (2H), 7.1 (1H), 7.4 (1H), 7.7–7.8 (2H), 7.9 (1H), 8.6 (1H), 9.05 (1H), 9.1 (1H), 10.3 (1H) ppm. MS: m/e=367 (M$^+$+H).

Example 54

2-(2-(Benzyloxy)pyridin-5-yl)benzimidazole-4-carboxamide

Synthesis took place in analogy to Example 49.
MS: m/e=345 (M$^+$+H).

Example 55

2-(2-(3-(N-Benzyl-N-methylamino)prop-1-yloxy)pyridin-5-yl)benzimidazole-4-carboxamide

Synthesis took place in analogy to Example 49.
MS: m/e=416 (M$^+$+H).

Example 56

2-(2-(3-(4-Methylpiperazin-1-yl)prop-1-yloxy)pyridin-5-yl)benzimidazole-4-carboxamide Synthesis took place in analogy to Example 49.
MS: m/e=395 (M$^+$+H).

Example 57

2-(2-(2-Piperidin-1-yleth-1-yloxy)pyridin-5-yl)benzimidazole-4-carboxamide

Synthesis took place in analogy to Example 49.
MS: m/e=366 (M$^+$+H).

Example 58

2-(2-(2-(N,N-Diethylamino)eth-1-yloxy)pyridin-5-yl)benzimidazole-4-carboxamide

Synthesis took place in analogy to Example 49.
MS: m/e=254 (M$^+$+H).

Example 59

2-(2-(4-Benzylaminophenyloxy)pyridin-5-yl)benzimidazole-4-carboxamide

Synthesis took place in analogy to Example 49.
MS: m/e=436 (M$^+$+H).

The synthesis of Examples 60–133 was carried out in automated parallel synthesis by the following general method:

Aldehyde (0.2 mmol) and 2,3-diaminobenzamide (0.2 mmol) were introduced together with Na$_2$S$_2$O$_5$ (0.26 mmol) into 5 ml of dimethylformamide and stirred at 140° C. for 2 h. The residue after removal of the solvent in vacuo was taken up in dichloromethane and washed with water and 1 N aqueous HCl. The aqueous HCl phase was neutralized with saturated sodium bicarbonate solution and extracted with dichloromethane. The organic phase was concentrated in vacuo, and the crude product was then purified by chromatography.

Example 60

2-(2-(4-Methylphenyl)oxazol-4-yl)benzimidazole-4-carboxamide

MS: m/e=319 (M$^+$+H).

Example 61

2-(1-(4-Fluorophenyl)-5-methylpyrazol-4-yl)benzimidazole-4-carboxamide

MS: m/e=336 (M$^+$+H).

Example 62

2-(1-(4-Chlorophenyl)pyrazol-5-yl)benzimidazole-4-carboxamide

MS: m/e=339 (M$^+$+H).

Example 63

2-(2-(4-Chlorophenyl)oxazol-4-yl)benzimidazole-4-carboxamide

MS: m/e=340 (M$^+$+H).

Example 64

2-(3-Propylisoxazol-5-yl)benzimidazole-4-carboxamide

MS: m/e=271 (M$^+$+H).

Example 65

2-(3-Ethyloxycarbonylpyrazol-5-yl)benzimidazole-4-carboxamide

MS: m/e=300 (M$^+$+H).

Example 66

2-(1-(4-Bromophenyl)pyrrol-3-yl)benzimidazole-4-carboxamide

MS: m/e=382 (M$^+$+H).

Example 67

2-((5-Acetyloxymethyl)furan-2-yl)benzimidazole-4-carboxamide

MS: m/e=300 (M$^+$+H).

Example 68

2-(N-Methylindol-3-yl)benzimidazole-4-carboxamide

MS: m/e=291 (M$^+$+H).

Example 69

2-Pyrrol-2-ylbenzimidazole-4-carboxamide

MS: m/e=227 (M$^+$+H).

Example 70

2-(2-Methyl-5-nitroindol-3-yl)benzimidazole-4-carboxamide

MS: m/e=338 (M$^+$+H).

Example 71

2-(N-Acetylindol-3-yl)benzimidazole-4-carboxamide

MS: m/e=319 (M$^+$+H).

Example 72

2-(5-Chloroindol-3-yl)benzimidazole-4-carboxamide

MS: m/e=311 (M$^+$+H).

Example 73

2-(1-(4-Methoxyphenyl)pyrrol-3-yl)benzimidazole-4-carboxamide

MS: m/e=333 (M$^+$+H).

Example 74

2-(1,2,5-Trimethylpyrrol-3-yl)benzimidazole-4-carboxamide

MS: m/e=269 (M$^+$+H).

Example 75

2-(2-Methylindol-3-yl)benzimidazole-4-carboxamide

MS: m/e=291 (M$^+$+H).

Example 76

2-(3-Phenylpyrazol-4-yl)benzimidazole-4-carboxamide

MS: m/e=304 (M$^+$+H).

Example 77

2-(6-Methoxycarbonylindol-3-yl)benzimidazole-4-carboxamide

MS: m/e=335 (M$^+$+H).

Example 78

2-(2-Ethylimidazol-4-yl)benzimidazole-4-carboxamide

MS: m/e=255 (M$^+$+H).

Example 79

2-(4-(2,6-Difluorophenyl-1-carbonyl)-1-methylpyrrol-2-yl)benzimidazole-4-carboxamide MS: m/e=381 (M$^+$+H).

Example 80

2-(4-(4-Fluorophenyl-1-carbonyl)-1-methylpyrrol-2-yl)benzimidazole-4-carboxamide MS: m/e=363 (M$^+$+H).

Example 81

2-(1-Methyl-4-(phenyl-1-carbonyl)pyrrol-2-yl)benzimidazole-4-carboxamide

MS: m/e=345 (M$^+$+H).

Example 82

2-(1-(4-Chlorophenyl)pyrrol-3-yl)benzimidazole-4-carboxamide

MS: m/e=338 (M$^+$+H).

Example 83

2-(2-(2,4-Dichlorophenyl)oxazol-4-yl)benzimidazole-4-carboxamide

MS: m/e=374 (M$^+$+H).

Example 84

2-(1-(2,4-Dichlorophenyl)-5-methylpyrazol-4-yl)benzimidazole-4-carboxamide

MS: m/e=387 (M$^+$+H).

Example 85

2-(2,5-Dibromothien-3-yl)benzimidazole-4-carboxamide

MS: m/e=402 (M$^+$+H).

Example 86

2-(2-Phenyloxazol-4-yl)benzimidazole-4-carboxamide

MS: m/e=305 (M$^+$+H).

Example 87

2-(3-Hydroxy-5-hydroxyethyl-2-methylpyridin-4-yl)benzimidazole-4-carboxamide

MS: m/e=299 (M$^+$+H).

Example 88

2-(1-(2,3,4-Trichlorophenyl)pyrrol-3-yl)benzimidazole-4-carboxamide

MS: m/e=407 (M$^+$+H).

Example 89

2-(Indol-3-yl)benzimidazole-4-carboxamide

MS: m/e=277 (M$^+$+H).

Example 90

2-(1-(4-Chloro-2-nitrophenyl)pyrrol-3-yl)benzimidazole-4-carboxamide

MS: m/e=385 (M$^+$+H).

Example 91

2-(6-Methylpyridin-2-yl)benzimidazole-4-carboxamide

MS: m/e=253 (M$^+$+H).

Example 92

2-(1-(Benzylaminocarbonylmethyl)pyrrol-2-yl)benzimidazole-4-carboxamide

MS: m/e=374 (M$^+$+H).

Example 93

2-(4-Methyl-5-(4-trifluormethylphenyl)isoxazol-3-yl)benzimidazole-4-carboxamide

MS: m/e=387 (M$^+$+H).

Example 94

2-(1-Phenylpyrazol-4-yl)benzimidazole-4-carboxamide

MS: m/e=304 (M$^+$+H).

Example 95

2-(1-(4-Chlorophenyl)pyrazol-4-yl)benzimidazole-4-carboxamide

MS: m/e=339 (M$^+$+H).

Example 96

2-(5-Methyl-1-phenylpyrazol-4-yl)benzimidazole-4-carboxamide

MS: m/e=318 (M$^+$+H).

Example 97

2-(1-(3-Cyano-4-methoxypyridin-2-yl)pyrrol-2-yl)benzimidazole-4-carboxamide

MS: m/e=359 (M$^+$+H).

Example 98

2-(1-(4-Tolylsulfonyl)indol-3-yl)benzimidazole-4-carboxamide

MS: m/e=431 (M$^+$+H).

Example 99

2-(5-Methoxyindol-3-yl)benzimidazole-4-carboxamide

MS: m/e=307 (M$^+$+H).

Example 100

2-(2-Phenylimidazol-4-yl)benzimidazole-4-carboxamide

MS: m/e=304 (M$^+$+H).

Example 101

2-(1-(2-nitrophenylsulfonyl)pyrrol-2-yl)benzimidazole-4-carboxamide

MS: m/e=412 (M$^+$+H).

Example 102

2-(4-Bromo-1-(4-chlorophenylmethyl)pyrazol-5-yl)benzimidazole-4-carboxamide

MS: m/e=431 (M$^+$+H).

Example 103

2-(2-(4-Fluorophenylcarbonyl)benzofuran-5-yl)benzimidazole-4-carboxamide

MS: m/e=400 (M$^+$+H).

Example 104

2-(1-(2,4-Difluorophenylsulfonyl)pyrrol-2-yl)benzimidazole-4-carboxamide

MS: m/e=403 (M$^+$+H).

Example 105

2-(1-(4-Methylphenyl)pyrrol-2-yl)benzimidazole-4-carboxamide

MS: m/e=317 (M$^+$+H).

Example 106

2-(4-(4-Chlorophenylcarbonyl)-1-methylpyrrol-2-yl)benzimidazole-4-carboxamide

MS: m/e=380 (M$^+$+H).

Example 107

2-(2-(4-Fluorophenyl)indol-3-yl)benzimidazole-4-carboxamide

MS: m/e=371 (M$^+$+H).

Example 108

2-(3,7-Dichloroquinolin-8-yl)benzimidazole-4-carboxamide

MS: m/e=358 (M$^+$+H).

Example 109

2-(5-Chloro-3-methyl-1-phenylpyrazol-4-yl)benzimidazole-4-carboxamide

MS: m/e=353 (M$^+$+H).

Example 110

2-(5-Methylfuran-2-yl)benzimidazole-4-carboxamide

MS: m/e=242 (M$^+$+H).

Example 111

2-(1-(2-Chlorophenyl)-5-trifluoromethylpyrazol-4-yl)benzimidazole-4-carboxamide

MS: m/e=407 (M$^+$+H).

Example 112

2-(1-(2,4-Dichlorophenyl)-5-trifluoromethylpyrazol-4-yl)benzimidazole-4-carboxamide MS: m/e=441 (M$^+$+H).

Example 113

2-(1-tert-Butylpyrazol-4-yl)benzimidazole-4-carboxamide

MS: m/e=284 (M$^+$+H).

Example 114

2-(5-Methylimidazol-4-yl)benzimidazole-4-carboxamide

MS: m/e=242 (M$^+$+H).

Example 115

2-(4-Chloro-5-nitrobenzothiophen-2-yl)benzimidazole-4-carboxamide

MS: m/e=374 (M$^+$+H).

Example 116

2-(1-Dimethylamino-3-methoxyisoquinolin-4-yl)benzimidazole-4-carboxamide

MS: m/e=362 (M$^+$+H).

Example 117

2-(1-Phthalimidobutylindol-3-yl)benzimidazole-4-carboxamide

MS: m/e=478 (M$^+$+H).

Example 118

2-(1-Methylpyrazol-4-yl)benzimidazole-4-carboxamide

MS: m/e=242 (M$^+$+H).

Example 119

2-(1-(2,6-Dimethylphenyl)pyrrol-3-yl)benzimidazole-4-carboxamide

MS: m/e=331 (M$^+$+H).

Example 120

2-(2-Dimethylaminothiazol-5-yl)benzimidazole-4-carboxamide

MS: m/e=288 (M$^+$+H).

Example 121

2-(1-tert-Butylpyrrol-3-yl)benzimidazole-4-carboxamide

MS: m/e=283 (M$^+$+H).

Example 122

2-(3-But-2-ylisoxazol-5-yl)benzimidazole-4-carboxamide

MS: m/e=285 (M$^+$+H).

Example 123

2-(3-iso-Butylisoxazol-5-yl)benzimidazole-4-carboxamide

MS: m/e=284 (M$^+$+H).

Example 124

2-(3-(4-tert-Butylphenyl)isoxazol-5-yl)benzimidazole-4-carboxamide

MS: m/e=361 (M$^+$+H).

Example 125

2-(3-tert-Butylisoxazol-5-yl)benzimidazole-4-carboxamide

MS: m/e=285 (M$^+$+H).

Example 126

2-(3-Phenylisoxazol-5-yl)benzimidazole-4-carboxamide

MS: m/e=305 (M$^+$+H).

Example 127

2-(3-tert-Butyl-5-phenylisoxazol-4-yl)benzimidazole-4-carboxamide

MS: m/e=361 (M$^+$+H).

Example 128

2-(1-(4-Chlorophenyl)-5-methylpyrazol-4-yl)benzimidazole-4-carboxamide

MS: m/e=353 (M$^+$+H).

Example 129

2-(1-(4-Chlorophenyl)-3-methylpyrazol-4-yl)benzimidazole-4-carboxamide

MS: m/e=353 (M$^+$+H).

Example 130

2-(1-(4-Bromophenyl)pyrazol-4-yl)benzimidazole-4-carboxamide

MS: m/e=383 (M$^+$+H).

Example 131

2-(1-(4-Chlorophenyl)-3,5-dimethylpyrazol-4-yl)benzimidazole-4-carboxamide

MS: m/e=366 (M$^+$+H).

Example 132

2-(1-(4-Methoxyphenyl)-5-trifluoromethylpyrazol-4-yl)benzimidazole-4-carboxamide MS: m/e=402 (M$^+$+H).

Example 133

2-(4-Methyl-5-phenylisoxazol-3-yl)benzimidazole-4-carboxamide

MS: m/e=319 (M$^+$+H).

The following compounds according to the invention can be prepared in analogy to the methods described above:
1. 2-pyridin-2-ylbenzimidazole-4-carboxamide
2. 2-(2-(2-(N,N-dimethylamino)eth-1-ylamino)pyridin-3-yl-benzimidazole-4-carboxamide
3. 2-(2-(2-pyrrolidin-1-yleth-1-ylamino)pyridin-3-yl)benzimidazole-4-carboxamide
4. 2-(2-(2-piperidin-1-yleth-1-ylamino)pyridin-3-yl)benzimidazole-4-carboxamide
5. 2-(2-(2-homopiperidin-1-yleth-1-ylamino)pyridin-3-yl)benzimidazole-4-carboxamide
6. 2-(2-(2-(4-phenylpiperidin-1-yl)eth-1-ylamino)pyridin-3-yl)benzimidazole-4-carboxamide
7. 2-(2-(2-piperazin-1-yl-eth-1-ylamino)pyridin-3-yl)benzimidazole-4-carboxamide
8. 2-(2-(2-(4-methylpiperazin-1-yl)eth-1-ylamino)pyridin-3-yl)benzimidazole-4-carboxamide
9. 2-(2-(2-(4-benzylpiperazin-1-yl)eth-1-ylamino)pyridin-3-yl)benzimidazole-4-carboxamide
10. 2-(2-(2-(N,N-dimethylamino)eth-1-yl)methylamino)pyridin-3-yl)benzimidazole-4-carboxamide
11. 2-(2-(2-pyrrolidin-1-yleth-1-yl)methylamino)pyridin-3-yl)benzimidazole-4-carboxamide
12. 2-(2-(2-piperidin-1-yleth-1-yl)methylamino)pyridin-3-yl)benzimidazole-4-carboxamide
13. 2-(2-(2-homopiperidin-1-yleth-1-yl)methylamino)pyridin-3-yl)benzimidazole-4-carboxamide
14. 2-(2-(2-(4-phenylpiperidin-1-yl)eth-1-yl)methylamino)pyridin-3-yl)benzimidazole-4-carboxamide
15. 2-(2-(2-piperazin-1-yleth-1-yl)methylamino)pyridin-3-yl)benzimidazole-4-carboxamide
16. 2-(2-(2-(4-methylpiperazin-1-yl)eth-1-yl)methylamino)pyridin-3-yl)benzimidazole-4-carboxamide
17. 2-(2-(2-(4-benzylpiperazin-1-yl)eth-1-yl)methylamino)pyridin-3-yl)benzimidazole-4-carboxamide
18. 2-(2-(3-(N,N-dimethylamino)prop-1-ylamino)pyridin-3-yl)benzimidazole-4-carboxamide
19. 2-(2-(3-pyrrolidin-1-ylprop-1-ylamino)pyridin-3-yl)benzimidazole-4-carboxamide
20. 2-(2-(3-piperidin-1-ylprop-1-ylamino)pyridin-3-yl)benzimidazole-4-carboxamide
21. 2-(2-(3-homopiperidin-1-ylprop-1-ylamino)pyridin-3-yl)benzimidazole-4-carboxamide 22. 2-(2-(3-(4-phenylpiperidin-1-yl)prop-1-ylamino)pyridin-3-yl)benzimidazole-4-carboxamide
23. 2-(2-(3-piperazin-1-ylprop-1-yl)pyridin-3-yl)benzimidazole-4-carboxamide
24. 2-(2-(3-(4-methylpiperazin-1-yl)prop-1-ylamino)pyridin-3-yl)benzimidazole-4-carboxamide
25. 2-(2-(3-(4-benzylpiperazin-1-yl)prop-1-ylamino)pyridin-3-yl)benzimidazole-4-carboxamide
26. 2-quinoxalin-2-ylbenzimidazole-4-carboxamide
27. 2-benzofuran-2-ylbenzimidazole-4-carboxamide
28. 2-benzotriazol-5-ylbenzimidazole-4-carboxamide
29. 2-thiazol-2-ylbenzimidazole-4-carboxamide
30. 2-pyridazin-4-ylbenzimidazole-4-carboxamide
31. 2-(1-(2-(N,N-diethylamino)eth-1-yl)pyrrol-2-yl)benzimidazole-4-carboxamide
32. 2-(4-hydroxypyridin-3-yl)benzimidazole-4-carboxamide
33. 2-(4-methoxypyridin-3-yl)benzimidazole-4-carboxamide
34. 2-(4-benzyloxypyridin-3-yl)benzimidazole-4-carboxamide
35. 2-(4-(2-(N,N-dimethylamino)eth-1-yloxy)pyridin-3-yl)benzimidazole-4-carboxamide
36. 2-(4-(2-(N,N-diethylamino)eth-1-yloxy)pyridin-3-yl)benzimidazole-4-carboxamide
37. 2-(4-(3-(N,N-dimethylamino)prop-1-yloxy)pyridin-3-yl)benzimidazole-4-carboxamide
38. 2-(4-(3-(N,N-diethylamino)prop-1-yloxy)pyridin-3-yl)benzimidazole-4-carboxamide
39. 2-(4-(2-pyrrolidin-1-yleth-1-yl)oxypyridin-3-yl)benzimidazole-4-carboxamide
40. 2-(4-(3-pyrrolidin-1-ylprop-1-yloxy)pyridin-3-yl)benzimidazole-4-carboxamide
41. 2-(4-(2-piperidin-1-yleth-1-yloxy)pyridin-3-yl)benzimidazole-4-carboxamide
42. 2-(4-(3-piperidin-1-ylprop-1-yloxy)pyridin-3-yl)benzimidazole-4-carboxamide
43. 2-(4-(2-piperazin-1-yleth-1-yloxy)pyridin-3-yl)benzimidazole-4-carboxamide
44. 2-(4-(3-piperazin-1-ylprop-1-yloxy)pyridin-3-yl)benzimidazole-4-carboxamide
45. 2-(4-(2-(4-methylpiperazin-1-yl)eth-1-yloxy)pyridin3-yl)benzimidazole-4-carboxamide
46. 2-(4-(3-(4-methylpiperazin-1-yl)prop-1-yloxy)pyridin3-yl)benzimidazole-4-carboxamide
47. 2-(4-(2-(4-benzylpiperazin-1-yl)eth-1-yloxy)pyridin-3-yl)benzimidazole-4-carboxamide
48. 2-(4-(3-(4-benzylpiperazin-1-yl)prop-1-yloxy)pyridin-3-yl)benzimidazole-4-carboxamide
49. 2-(4-(4-methylpiperazin-1-yl)pyridin-3-yl)benzimidazole-4-carboxamide
50. 2-(4-(4-benzylpiperazin-1-yl)pyridin-3-yl)benzimidazole-4-carboxamide
51. 2-(4-(4-ethylpiperazin-1-yl)pyridin-3-yl)benzimidazole-4-carboxamide
52. 2-(4-(4-butylpiperazin-1-yl)pyridin-3-yl)benzimidazole-4-carboxamide
53. 2-(6-(3-(N,N-dimethylamino)prop-1-ylamino)pyridin-3-yl)benzimidazole-4-carboxamide
54. 2-(6-((3-(N,N-dimethylamino)prop-1-yl)methylamino)pyridin-3-yl)benzimidazole-4-carboxamide
55. 2-(6-(2-(N,N-dimethylamino)-eth-1-ylamino)pyridin-3-yl)benzimidazole-4-carboxamide
56. 2-(6-((2-(N,N-dimethylamino)eth-1-yl)methylamino)pyridin-3-yl)benzimidazole-4-carboxamide
57. 2-(6-(3-(piperazin-1-yl)prop-1-ylamino)pyridin-3-yl)benzimidazole-4-carboxamide
58. 2-(6-(3-(4-ethylpiperazin-1-yl)prop-1-ylamino)pyridin-3-yl)benzimidazole-4-carboxamide
59. 2-(6-(3-(4-benzylpiperazin-1-yl)prop-1-ylamino)pyridin-3-yl)benzimidazole-4-carboxamide
60. 2-(6-((3-(piperazin-1-yl)prop-1-yl)methylamino)pyridin-3-yl)benzimidazole-4-carboxamide
61. 2-(6-((3-(4-ethylpiperazin-1-yl)prop-1-yl)methylamino)pyridin-3-yl)benzimidazole-4-carboxamide
62. 2-(6-((3-(4-benzylpiperazin-1-yl)prop-1-yl)methylamino)pyridin-3-yl)benzimidazole-4-carboxamide
63. 2-(6-(3-(homopiperazin-1-yl)prop-1-ylamino)pyridin-3-yl)benzimidazole-4-carboxamide
64. 2-(6-(3-(4-methylhomopiperazin-1-yl)prop-1-ylamino)pyridin-3-yl)benzimidazole-4-carboxamide
65. 2-(6-(3-(4-ethylhomopiperazin-1-yl)prop-1-ylamino)pyridin-3-yl)benzimidazole-4-carboxamide
66. 2-(6-(3-(4-benzylhomopiperazin-1-yl)prop-1-ylamino)pyridin-3-yl)benzimidazole-4-carboxamide
67. 2-(6-((3-(homopiperazin-1-yl)prop-1-yl)methylamino)pyridin-3-yl)benzimidazole-4-carboxamide
68. 2-(6-((3-(4-methylhomopiperazin-1-yl)prop-1-yl)methylamino)pyridin-3-yl)benzimidazole-4-carboxamide
69. 2-(6-((3-(4-ethylhomopiperazin-1-yl)prop-1-yl)methylamino)pyridin-3-yl)benzimidazole-4-carboxamide
70. 2-(6-((3-(4-benzylhomopiperazin-1-yl)prop-1-yl)methylamino)pyridin-3-yl)benzimidazole-4-carboxamide
71. 2-(6-(2-(piperazin-1-yl)eth-1-ylamino)pyridin-3-yl)benzimidazole-4-carboxamide
72. 2-(6-(2-(4-methylpiperazin-1-yl)eth-1-ylamino)pyridin-3-yl)benzimidazole-4-carboxamide
73. 2-(6-(2-(4-ethylpiperazin-1-yl)eth-1-ylamino)pyridin-3-yl)benzimidazole-4-carboxamide
74. 2-(6-(2-(4-benzylpiperazin-1-yl)eth-1-ylamino)pyridin-3-yl)benzimidazole-4-carboxamide
75. 2-(6-((2-(piperazin-1-yl)eth-1-yl)methylamino)pyridin-3-yl)benzimidazole-4-carboxamide
76. 2-(6-((2-(methylpiperazin-1-yl)eth-1-yl)methylamino)pyridin-3-yl)benzimidazole-4-carboxamide
77. 2-(6-((2-(4-ethylpiperazin-1-yl)eth-1-yl)methylamino)pyridin-3-yl)benzimidazole-4-carboxamide
78. 2-(6-((2-(4-benzylpiperazin-1-yl)eth-1-yl)methylamino)pyridin-3-yl)benzimidazole-4-carboxamide
79. 2-(6-(2-(homopiperazin-1-yl)eth-1-ylamino)pyridin-3-yl)benzimidazole-4-carboxamide
80. 2-(6-(2-(4-methylhomopiperazin-1-yl)eth-1-ylamino)pyridin-3-yl)benzimidazole-4-carboxamide
81. 2-(6-(2-(4-ethylhomopiperazin-1-yl)eth-1-ylamino)pyridin-3-yl)benzimidazole-4-carboxamide
82. 2-(6-(2-(4-benzylhomopiperazin-1-yl)eth-1-ylamino)pyridin-3-yl)benzimidazole-4-carboxamide
83. 2-(6-((2-(homopiperazin-1-yl)eth-1-yl)methylamino)pyridin-3-yl)benzimidazole-4-carboxamide
84. 2-(6-((2-(4-methylhomopiperazin-1-yl)eth-1-yl)methylamino)pyridin-3-yl)benzimidazole-4-carboxamide
85. 2-(6-((2-(4-ethylhomopiperazin-1-yl)eth-1-yl)methylamino)pyridin-3-yl)benzimidazole-4-carboxamide
86. 2-(6-((2-(4-benzylhomopiperazin-1-yl)eth-1-yl)methylamino)pyridin-3-yl)benzimidazole-4-carboxamide
87. 2-(6-(homopiperazin-1-yl)pyridin-3-yl)benzimidazole-4-carboxamide
88. 2-(6-(4-methylhomopiperazin-1-yl)pyridin-3-yl)benzimidazole-4-carboxamide
89. 2-(6-(4-ethylhomopiperazin-1-yl)pyridin-3-yl)benzimidazole-4-carboxamide
90. 2-(6-(4-propylhomopiperazin-1-yl)pyridin-3-yl)benzimidazole-4-carboxamide
91. 2-(6-(4-butylhomopiperazin-1-yl)pyridin-3-yl)benzimidazole-4-carboxamide 92. 2-(6-(4-tert-butylhomopiperazin-1-yl)pyridin-3-yl)benzimidazole-4-carboxamide
93. 2-(6-(4-phenylhomopiperazin-1-yl)pyridin-3-yl)benzimidazole-4-carboxamide
94. 2-(6-(4-benzylhomopiperazin-1-yl)pyridin-3-yl)benzimidazole-4-carboxamide
95. 2-(6-(homopiperidin-1-yl)pyridin-3-yl)benzimidazole-4-carboxamide
96. 2-(6-(morpholine-4-yl)pyridin-3-yl)benzimidazole-4-carboxamide.

We claim:
1. A compound of the formula I or II

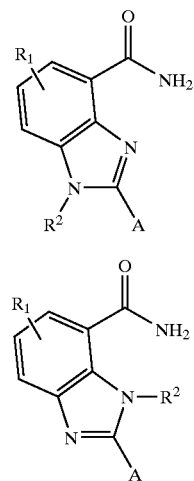

in which
A is naphthalene, a monocyclic aromatic, bicyclic and tricyclic aromatic or partly aromatic heterocyclic system comprising a maximum of 15 carbon atoms and up to 4 beteroatoms selected from the group of N,O,S, and rings may additionally carry up to 2 oxo groups, and A may also be substituted by up to three different or identical $R^3$ radicals and additionally one $R^4$ radical, and $R^1$ is hydrogen, chlorine, fluorine, bromine, iodine, branched and unbranched $C_1$–$C_6$-alkyl, OH, nitro, $CF_3$, CN, $NR^{11}R^{12}$, NH—CO—$R^{13}$, O—$C_1$–$C_4$-alkyl, where $R^{11}$ and $R^{12}$ are, independently of one another, hydrogen or $C_1$–$C_4$-alkyl, and $R^{13}$ is hydrogen, $C_1$–$C_4$-alkyl, phenyl-$C_1$–$C_4$-alkyl or phenyl, and $R^2$ is hydrogen, branched and unbranched $C_1$–$C_6$-alkyl and $R^3$ is hydrogen, chlorine, bromine, iodine, fluorine, $CF_3$, $OCF_3$, nitro, $NH_2$, CO—$R^8$, $CO_2$—$R^8$, $SO_2$—$R^8$, OH, O—$C_1$–$C_4$-alkyl, phenyl-$C_0$–$C_4$-alkyl-O—, a $C_1$–$C_6$ chain which may be saturated, unsaturated or partially unsaturated and may also be substituted by an $R^{33}$ radical, phenyl, where the phenyl rings may also be substituted by up to three identical or different $R^{31}$ radicals, and pyridyl which may be substituted by up to three $R^{32}$ radicals, and $R^{31}$ is OH, $C_1$–$C_6$-alkyl, O—$C_1$–$C_4$-alkyl, chlorine, bromine, iodine, fluorine, $CF_3$, nitro, $NH_2$, and $R^{32}$ is OH, $C_1$–$C_6$-alkyl, O—$C_1$–$C_4$-alkyl, chlorine, bromine, iodine, fluorine, $CF_3$, nitro, $NH_2$, CN, and $R^{33}$ is CO—NH—$R^8$, OH, O—$C_1$–$C_6$-Alkyl, O—CO—$R^8$, and $R^4$ is hydrogen and —(D)$_p$—(E)$_s$—(CH$_2$)$_q$—B, where D is S, $NR^{43}$ and O
E is phenyl and
s is 0 and 1 and
B is $NR^{41}R^{42}$ and

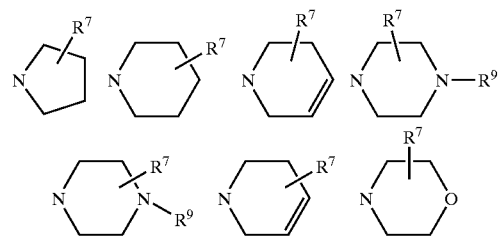

and
p can be 0 and 1, and
q can be 0, 1, 2, 3 or 4, and
$R^{41}$ can be hydrogen, $C_1$–$C_6$-alkyl, (CH$_2$)$_r$—G, and
$R^{42}$ can be hydrogen, $C_1$–$C_6$-alkyl, —CO—$R^8$, $SO_2$—$R^8$, $CO_2$—$R^8$, —(C=NH)—$R^8$ and —(C=NH)—$NHR^8$ and
$R^{41}$ and $R^{42}$ can form a phthaloyl radical and
$R^{43}$ can be hydrogen and $C_1$–$C_4$-alkyl and
r can be 0,1,2,3,4 and
G can be phenyl, which may also carry a maximum of two radicals $NR^{11}R^{12}$, phenyl-$C_1$–$C_4$-alkyl-NH, pyrrolidine, piperidine, 1,2,5,6-tetrahydropyridine, morpholine, homopiperidine, piperazine, which may also be substituted by an alkyl radical $C_1$–$C_6$-alkyl, and homopiperazine, which may also be substituted by an alkyl radical $C_1$–$C_6$-alkyl, and
$R^7$ can be hydrogen, $C_1$–$C_6$-alkyl, phenyl, it also being possible for the ring to be substituted by up to two $R^{71}$ radicals, and
$R^{71}$ can be OH, $C_1$–$C_6$-alkyl, O—$C_1$–$C_4$-alkyl, chlorine, bromine, iodine, fluorine, $CF_3$, nitro, $NH_2$, and
$R^8$ can be $C_1$–$C_6$-alkyl, $CF_3$, $NR^{11}R^{12}$, phenyl, phenyl-$C_1$–$C_4$-alkyl, it also being possible for the ring to be substituted by up to two $R^{81}$ radicals, and
$R^{81}$ can be OH, $C_1$–$C_6$-alkyl, O—$C_1$–$C_4$-alkyl, chlorine, bromine, iodine, fluorine, $CF_3$, nitro, $NH_2$, and
$R^9$ can be hydrogen, CO—$R^8$, $SO_2$—$R^8$, $CO_2$—$R^8$, $C_1$–$C_6$-alkyl, phenyl-$C_1$–$C_4$-alkyl and phenyl, it being possible for the phenyl rings also to be substituted by up to two $R^{91}$ radicals, and
$R^{91}$ can be OH, $C_1$–$C_6$-alkyl, O—$C_1$–$C_4$-alkyl, chlorine, bromine, iodine, fluorine, $CF_3$, nitro, $NH_2$, and its tautomeric forms, possible enantiomeric and diastereomeric forms, and its phosphate, carbamate of amino acid or ester prodrugs.

2. A compound of claim 1, where
$R^1$ can be hydrogen and
$R^2$ can be hydrogen and $C_1$–$C_4$-alkyl and
D can be $NR^{43}$ and 0 and
p can be 0 and 1 and
s can be 0 and
q can be 0, 1 and 2, when p is 0 or q can be 2 and 3 when p is 1, and
$R^{42}$ and $R^{43}$ can be, independently of one another, hydrogen and $C_1$–$C_4$-alkyl and
$R^7$ can be hydrogen and phenyl and R⁹ can be hydrogen, $C_1$–$C_4$-alkyl and phenyl —$C_0$—$C_4$-alkyl.

3. A compound of claim 1, where A is selected from the group consisting of indole, benzimidazole, pyrrole, imidazole, furan, thiophene, benzothiophene, benzofuran, pyrazole, thiazole, benzothiazole, phthalimide, indazole, benzotriazole, phthalazine, indoline, isoindoline, pyridine, quinoline, pyrimidine, pyridazine, isoquinoline, quinoxaline, quinazoline, naphthalene, isoxazole, oxazole, imidazopyridine and pyrazine.

4. A compound of claim 2, where A is selected from the group consisting of pyridine, thiophene, thiazole, furan, indole, oxazole, pyrazole, pyrrole, benzofuran, imidazole, benzothiophene, isoxazole, pyrazine, pyrimidine, pyridazine, quinoline which may be substituted by up to three $R^3$ radicals and one R4 radical, where $R^3$ is selected from the group consisting of hydrogen, chlorine, bromine, iodine, fluorine, $COR^8$, $RO_2R^8$, $SO_2R^8$, phenyl —$C_1$-$C_4$-alkyl, a $C_1$–$C_6$ chain which may be saturated, unsaturated or partially unsaturated and may also be substituted by an O—CO—$R^8$ group, phenyl where the phenyl rings may also be substituted by up to three identical or different $R^{31}$ radicals and pyridyl which may be substituted by up to three identical or different $R^{32}$ radicals, and $R^4$ is hydrogen or $(D)_p$—$(E)_s$—$(CH_2)_q$—B, and $R^3$ and $R^4$ are not both hydrogen.

5. A compound of claim 2, where A is selected from the group consisting of pyridine, pyrazine, pyrimidine, pyridazine, quinoline, thiazole, thiophene, pyrrole and pyrazole which may be substituted by an $R^3$ radical and an $R^4$ radical, where $R^3$ is hydrogen, chlorine, bromine, iodine, fluorine or $C_1$–$C_4$-alkyl, and $R^4$ is $(D)_p$—$(E)_s$—$(CH_2)_q$—B.

6. A compound of claim 2, where A is selected from the group consisting of pyridine, thiophene and thiazole, which are substituted by an $R^4$ radical where $R^4$ is $(D)_p$—$(E)_s$—$(CH_2)_q$—B, and $R^3$ is hydrogen.

7. A drug composition comprising at least one compound of claim 1 in addition to conventional carriers and excipients.

8. A method of treating neurodegenerative disorders or neuronal damage caused by craniocerebral trauma comprising administering an effective amount of a compound of claim 1 to a patient in need of such treatment.

9. A method of treating neurodegenerative disorders or neuronal damage caused by ischemia, trauma or massive bleeding comprising administering an effective amount of a compound of claim 1 to a patient in need of such treatment.

10. The method of claim 8 wherein the disorder or damage is caused by Huntington's disease.

11. A method of treating or preventing damage due to ischemia comprising administering an effective amount of a compound of claim 1 to a patient in need of such treatment.

12. A method of treating epilepsy comprising administering an effective amount of a compound of claim 1 to a patient in need of such treatment.

13. A method of treating damage to the kidneys after renal ischemia or during and after kidney transplants comprising administering an effective amount of a compound of claim 1 to a patient in need of such treatment.

14. A method of treating damage to the heart after cardiac ischemia comprising administering an effective amount of a compound of claim 1 to a patient in need of such treatment.

15. A method of treating microinfarcts comprising administering an effective amount of a compound of claim 1 to a patient in need of such treatment.

16. A method of treating conditions associated with revascularization of critically narrowed coronary arteries comprising administering an effective amount of a compound of claim 1 to a patient in need of such treatment.

17. A method of treating acute myocardial infarct and damage during and after medical or mechanical lysis comprising administering an effective amount of a compound of claim 1 to a patient in need of such treatment.

18. A method of treating rheumatoid arthritis comprising administering an effective amount of a compound of claim 1 to a patient in need of such treatment.

19. A method of treating diabetes mellitus comprising administering an effective amount of a compound of claim 1 to a patient in need of such treatment.

20. The method of claim 12 wherein the epilepsy is petit mal seizures, tonoclonic seizures, temporal lobe seizures or complex partial seizures.

21. The method of claim 15 wherein the microinfarcts relate to heart valve replacement, aneurysm resections or heart transplants.

22. The method of claim 16 wherein the conditions are associated with Percutaneous Transluminal Coronary Angioplasty, bypass operations or critically narrowed articles.

* * * * *